United States Patent
Bassler et al.

(10) Patent No.: US 8,535,689 B2
(45) Date of Patent: Sep. 17, 2013

(54) IDENTIFICATION OF BACTERIAL AUTOINDUCER AND USE IN TREATING BACTERIAL PATHOGENICITY

(75) Inventors: Bonnie Bassler, Princeton, NJ (US); Martin Semmelhack, Princeton, NJ (US); Douglas A. Higgins, Point Pleasant, NJ (US); Megan Eileen Bolitho, San Mateo, CA (US); Kristina M. Kraml, Princeton, NJ (US); Wai-Leung Ng, Lawrenceville, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 316 days.

(21) Appl. No.: 12/681,041

(22) PCT Filed: Oct. 1, 2008

(86) PCT No.: PCT/US2008/011336
§ 371 (c)(1),
(2), (4) Date: May 6, 2010

(87) PCT Pub. No.: WO2009/088402
PCT Pub. Date: Jul. 16, 2009

(65) Prior Publication Data
US 2010/0273890 A1  Oct. 28, 2010

Related U.S. Application Data

(60) Provisional application No. 60/976,587, filed on Oct. 1, 2007, provisional application No. 61/189,844, filed on Aug. 22, 2008.

(51) Int. Cl.
*A61K 39/106* (2006.01)
*A61K 31/121* (2006.01)
*A61K 31/12* (2006.01)
*C07C 49/11* (2006.01)
*C07C 49/16* (2006.01)

(52) U.S. Cl.
USPC ........ 424/261.1; 514/676; 514/675; 514/678; 514/738; 435/148; 435/252.1; 564/502; 568/308; 568/382; 568/412; 568/419; 568/852

(58) Field of Classification Search
USPC .............. 424/261.1; 514/676, 675, 378, 738; 435/148, 252.1; 564/502; 568/308, 382, 568/412, 419, 852
See application file for complete search history.

(56) References Cited

U.S. PATENT DOCUMENTS

| | | |
|---|---|---|
| 6,365,709 B1 | 4/2002 | Heibel et al. |
| 2004/0033548 A1 | 2/2004 | Bassler et al. |
| 2004/0180829 A1 | 9/2004 | Bassler et al. |

FOREIGN PATENT DOCUMENTS

| | | |
|---|---|---|
| WO | 2004041781 A1 | 5/2004 |

OTHER PUBLICATIONS

Higgins et al. (Abstract MEDI 14 in ASC published abstracts on Jul. 25, 2007, pp. 8-9).*

(Continued)

*Primary Examiner* — Savitha Rao
(74) *Attorney, Agent, or Firm* — Meagher Emanuel Laks Goldberg & Bovino, LLP

(57) ABSTRACT

A bacterial autoinducer, CAI-1, was purified and its structure identified. Methods for synthesis of the autoinducer and its analogues were elucidated. Methods of using the autoinducer or its analogues for treating bacterial pathogenicity and bio film formation are described. Methods for prevention and treatment of cholera are described. Synthetic (S)-3-hydroxytridecan-4-one functions as well as natural CAI-1 in repressing production of the virulence factor toxin co-regulated pilus (TCP). Strategies are described to manipulate bacterial quorum sensing in the clinical arena.

14 Claims, 21 Drawing Sheets

(56) References Cited

OTHER PUBLICATIONS

Ritchie, Kim, B., "Regulation of Microbial Populations by Coral Surface Mucus and Mucus-Associated Bacteria", Mar Ecol Prog Ser 322:1-14 (2006).
Henke et al., "Three Parallel Quorum-Sensing Systems Regulate Gene Expression in *Vibrio harveyi*", J Bacter 186 (20):6902-6914 (2004).
Miller et al., "Parallel Quorum Sensing Systems Converge to Regulate Virulence in *Vibrio cholerae*", Aug. 9, 2002, Cell, vol. 110, pp. 303-314.
Zhu et al., "Quorum-sensing regulators control virulence gene expression in *Vibrio cholerae*", Mar. 5, 2002, PNAS, vol. 99, No. 5, pp. 3129-3134.
Chen et al., "Structural identification of a bacterial quorum-sensing signal containing boron", Jan. 31, 2002, Nature, vol. 415, pp. 545-549.
Miller et al., "Quorum Sensing in Bacteria", 2001, Annual Review of Microbiology, vol. 55, pp. 165-199.
Waters et al., "Quorum Sensing: Cell-to-Cell Communication in Bacteria", 2005, Annual Review of Cell and Developmental Biology, vol. 21, pp. 319-346.
Davies et al., "The Involvement of Cell-to-Cell Signals in the Development of a Bacterial Biofilm", Apr. 10, 1998, Science, vol. 280, pp. 295-298.
Passador et al., "Expression of *Pseudomonas aeruginosa* Virulence Genes Requires Cell-to-Cell Communication", May 21, 1993, Science, vol. 260, pp. 1127-1130.
Eberhard et al., "Structural Identification of Autoinducer of *Photobacterium fischeri* Luciferase", 1981, Biochemistry, vol. 20, pp. 2444-2449.
Solomon et al., "Purification and characterization of an extracellular peptide factor that affects two different developmental pathways in *Bacillus subtilis*", Aug. 30, 2012, Genes & Development, vol. 10, pp. 2014-2024.
Ren et al., "Stationary-Phase Quorum-Sensing Signals Affect Autoinducer-2 and Gene Expression in *Escherichia coli*", Apr. 2004, Applied and Environmental Microbiology, vol. 70, No. 4, pp. 2038-2043.
Xavier et al., "LuxS quorum sensing: more than just a numbers game", 2003, Current Opinion in Microbiology, vol. 6, pp. 191-197.
Schauder et al., "The LuxS family of bacterial autoinducers: biosynthesis of a novel quorum-sensing signal molecule", 2001, Molecular Microbiology, vol. 41, pp. 463-476.
Miller et al., "*Salmonella typhimurium* Recognizes a Chemically Distinct Form of the Bacterial Quorum-Sensing Signal AI-2", Sep. 10, 2004, Molecular Cell, vol. 15, pp. 677-687.
Hammer et al., "Quorum sensing controls biofilm formation in *Vibrio cholerae*", 2003, Molecular Microbiology, vol. 50, pp. 101-114.
Zhu et al., "Quorum Sensing-Dependent Biofilms Enhance Colonization in *Vibrio cholerae*", Oct. 2003, Developmental Cell, vol. 5, pp. 647-656.
Taylor et al., "Use of phoA gene fusions to identify a pilus colonization factor coordinately regulated with cholera toxin", May 1987, Genetics, vol. 84, pp. 2833-2837.
Neiditch et al., "Ligand-Induced Asymmetry in Histidine Sensor Kinase Complex Regulates Quorum Sensing", Sep. 22, 2006, Cell, vol. 126, pp. 1095-1108.
Eliot et al., "Pyridoxal Phosphate Enzymes: Mechanistic, Structural, and Evolutionary Considerations", 2004, Annu. Rev. Biochem., pp. 383-415.
Taga et al., "Chemical communication among bacteria", Nov. 25, 2003, PNAS, vol. 100, suppl. 2, pp. 14549-14554.
Pesci et al., "Quinolone signaling in the cell-to-cell communication system of *Pseudomonas aeruginosa*", Sep. 1999, Biochemistry, vol. 96, pp. 11229-11234.
Horinouchi et al., "A-factor as a microbial hormone that controls cellular differentiation and secondary metabolism in *Streptomyces griseus*", 1994, Molecular Microbiology, vol. 12, pp. 859-864.
Hall et al., "Identification of Components of Male-Produced Pheromone of Coffee White Stemborer, *Xylotrechus quadripes*", Jan. 2006, Journal of Chemical Ecology, vol. 32, No. 1, pp. 195-219.
Sack et al., "Cholera", Jan. 17, 2004, The Lancet, vol. 363, pp. 223-233.
Hammer et al., "Regulatory small RNAs circumvent the conventional quorum sensing pathway in pandemic *Vibrio cholerae*", Jul. 3, 2007, PNAS, vol. 104, No. 27, pp. 11145-11149.
Jia et al., "Mechanistic Studies on Class I Polyhydroxybutyrate (PHB) Synthase from *Ralstonia eutropha*: Class I and III Synthases Share a Similar Catalytic Mechanism", 2001, Biochemistry, vol. 40, No. 4, pp. 1011-1019.
Coutts et al., "A Stereospecific Synthesis of 24(S)-Hydroxyvitamin D2, a Prodrug for 1alpha, 24(S)-Dihydroxyvitamin D2", 2002, Organic Process Research & Development, vol. 6, pp. 246-255.
Barrow et al., "Synthesis of 1-Aza-cryptophycin 1, an Unstable Cryptophycin. An Unusual Skeletal Rearrangement", 2000, Tetrahedron, vol. 56, pp. 3339-3351.
Defoirdt et al., "Quorum sensing and quorum quenching in *Vibrio harveyi*: lessons learned from in vivo work", 2008, The ISME Journal, vol. 2, pp. 19-26.
Spirig et al., "The *Legionella* Autoinducer Synthase LqsA Produces an alpha-Hydroxyketone Signaling Molecule", Jun. 27, 2008, The Journal of Biological Chemistry, vol. 283, No. 26, pp. 18113-18123.

\* cited by examiner a.

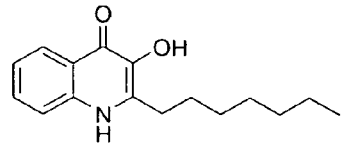
Pseudomonas Quinolone Signal (PQS)
(*Pseudomonas aeruginosa*)[20]

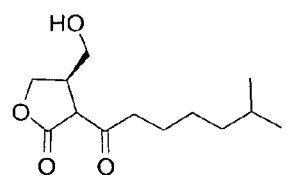
γ-Butyrolactone (A-factor)
(*Streptomyces griseus*)[21]

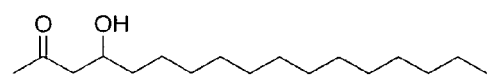
3-Hydroxypalmitic acid methyl ester
(3OH PAME) (*Ralstonia solanacearum*)[22]

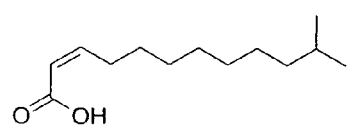
Diffusible Signal Factor (DSF)
(*Xanthomonas campestris* pv. *campestris*)[23]

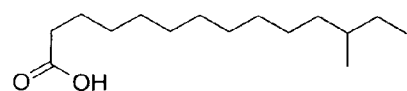
Diffusible Signal Factor (DSF)
(*Xylella fastidiosa*)[24]

b.

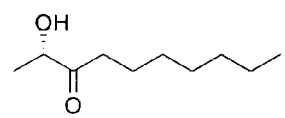
(*S*)-2-hydroxydecan-3-one
(*Xylotrechus quadripes* Chevrolat)[25]

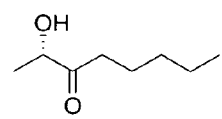
(*S*)-2-hydroxyoctan-3-one
(*Xylotrechus pyrrhoderus* Bates)[26]

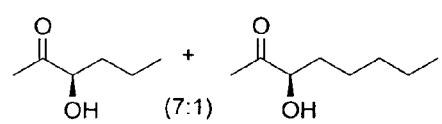
(*R*)-3-hydroxyhexan-2-one and (*R*)-3-hydroxyoctan-2-one
(*Anaglyptus subfasciatus*)[27]

Figure 5 a.) TBDPSCl, imidazole, DMF; then $K_2CO_3/H_2O$, 3:2 MeOH:THF; b.) 1,1'-carbonyldiimidazole;
then imidazole, 4-DMAP, HNMe(OMe)HCl, DCM; c.) RMgBr, THF; d.) TBAF, THF

| ANALOG NUMBER | ANALOG STRUCTURE | CHEMICAL NAME | APPROX % OF CAI-1 ACTIVITY | REFERENCES |
|---|---|---|---|---|
| CAI-1 | | (S)-3-hydroxytridecan-4-one (CAI-1) | 100 | 11 (racemic mix) |
| 1 | | 3-hydroxyheptan-4-one | <1 | 1-7 (racemic & R) |
| 2 | | 3-hydroxynonan-4-one | <1 | none |
| 3 | | (S)-3-hydroxyundecan-4-one | 4 | none |
| 4 | | (R)-3-hydroxyundecan-4-one | 2 | none |
| 5 | | (S)-3-hydroxydodecan-4-one | 20 | 8-10 (racemic) |
| 6 | | (R)-3-hydroxydodecan-4-one | 20 | 8-10 (racemic) |
| 7 | | (R)-3-hydroxytridecan-4-one | 40 | 11 (racemic mix) |

Figure 13a

CAI-1 ANALOGS AND SYNTHETIC PRECURSORS

| # | Structure | Name | | |
|---|---|---|---|---|
| 8 | 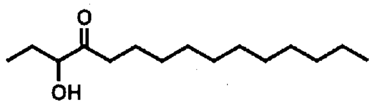 | 3-hydroxypentadecan-4-one {LAI-1} | <1 | 12 |
| 9 | 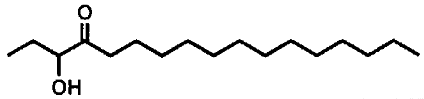 | 3-hydroxyheptadecan-4-one | <1 | none |
| 10 | 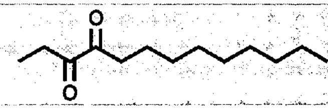 | tridecane-3,4-dione | 10 | none |
| 11 | 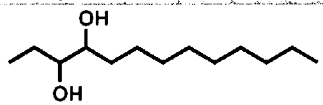 | tridecane-3,4-diol | 7 | none |
| 12 | 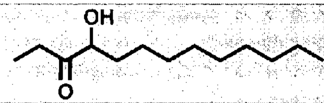 | 4-hydroxytridecan-3-one | 2 | 11 |
| 13 | 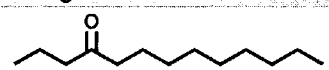 | tridecan-4-one | 2 | commercial |
| 14 | 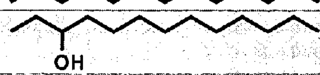 | tridecan-3-ol | <1 | commercial |
| 15 | 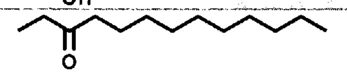 | tridecan-3-one | <1 | commercial |
| 16 | 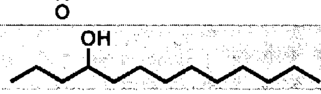 | tridecan-4-ol | <1 | commercial |
| 17 | 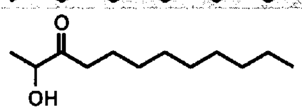 | 2-hydroxydodecan-3-one | | 13 |
| 18 | 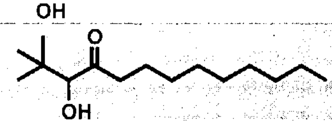 | 3-hydroxy-2,2-dimethyltridecan-4-one | <1 | none |

Figure 13b

CAI-1 ANALOGS AND SYNTHETIC PRECURSORS

| # | Structure | Name | Activity | Compound # |
|---|---|---|---|---|
| 19 | 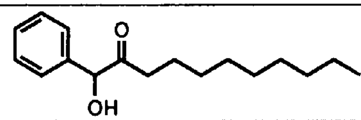 | 1-hydroxy-1-phenylundecan-2-one | <1 | 14 |
| 20 | 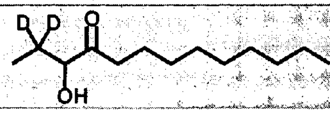 | 2,2-D₂-3-hydroxytridecan-4-one | 100 | none |
| 21 | 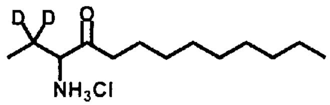 | 2,2-D₂-3-(chloroamino)tridecan-4-one | | none |
| 22 | 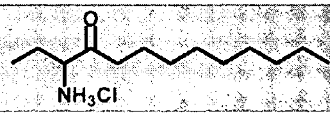 | 3-(chloroamino)tridecan-4-one | 100 | none |
| 23 | 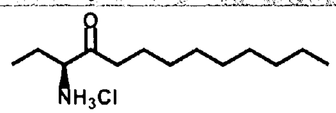 | (S)-3-(chloroamino)tridecan-4-one | | none |
| 24 | 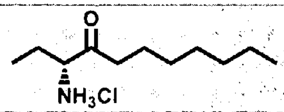 | (R)-3-(chloroamino)undecan-4-one | | none |
| 25 | 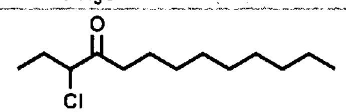 | 3-chlorotridecan-4-one | | none |
| 26 | 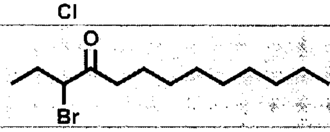 | 3-bromotridecan-4-one | | none |
| 27 | 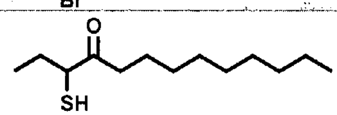 | 3-mercaptotridecan-4-one | | none |

Figure 13c

CAI-1 ANALOGS AND SYNTHETIC PRECURSORS

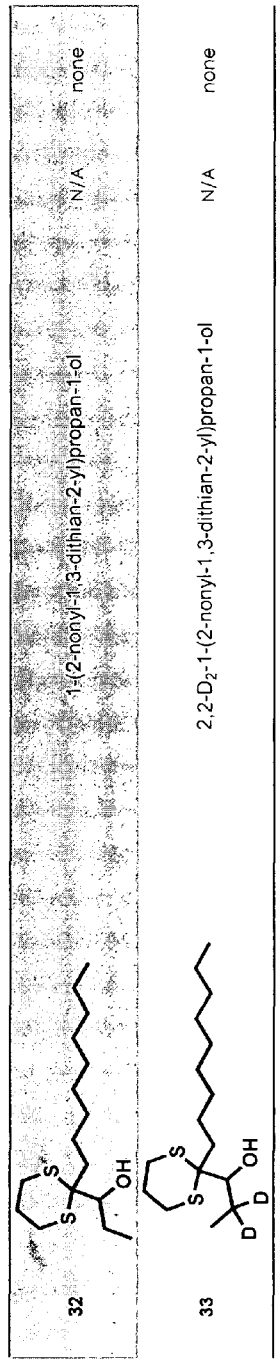

| | | |
|---|---|---|
| 32 | 1-(2-nonyl-1,3-dithian-2-yl)propan-1-ol | none |
| 33 | 2,2-D$_2$-1-(2-nonyl-1,3-dithian-2-yl)propan-1-ol | none |

REFERENCES:

1. Utsukihara, T.; Okada, S.; Kato, N.; Horiuchi, C.A. Journal of Molecular Catalysis B: Enzymatic. (2007), 45(1-2), 68-72. (RACEMIC)
2. Utsukihara, T.; Nakamura, H.; Watanabe, M.; Horiuchi, C.A. Tetrahedron Letters. (2006), 47(52), 9359-9364. (RACEMIC)
3. El-Qisairi, A.K.; Qaseer, H.A. Journal of Organometallic Chemistry. (2002), 659(1-2), 50-55. (RACEMIC)
4. Strobel, M.-P.; Morin, L.; Paquer, D. Nouveau Journal de Chimie. (1980), 4(10), 603-8. (RACEMIC)
5. Strobel, M.-P.; Morin, L.; Paquer, D. Tetrahedron Letters. (1980), 21(6), 523-4. (RACEMIC)
6. Lohray, B.B.; Enders, D. Helvetica Chimica Acta. (1989), 72, 980-984. (R)
7. Kroutil, et al. Journal of the Chemical Society: Perkin Transactions I. (1997), 24, 3629.
8. Collin, J.; Namy, J.-L.; Dallemer, F.; Kagan, H.B. Journal of Organic Chemistry. (1991), 56, 3118-3122. (RACEMIC)
9. Souppe, J.; Namy, J.-L.; Kagan, H.B. Tetrahedron Letters. (1984), 25(27), 2869-2872. (RACEMIC)
10. Namy, J.L.; Colomb, M.; Kagan, H.B. Tetrahedron Letters. (1994), 35(11), 1723-1726. (RACEMIC)
11. Heck, R.; Henderson, A.P.; Kohler, B.; Retey, J.; Golding, B.T. European Journal of Organic Chemistry. (2001), 2623-2627. (RACEMIC MIX)
12. Spirig, T.; Tiaden, A.; Kiefer, P.; Buchrieser, C.; Vorholt, J.A.; Hilbi, H. Journal of Biological Chemistry. 283(26), 18113-18123.
13. Abe, et al. Yukagaku. (1971), 20(4), 224.
14. Oshima, K.; Shimoji, K.; Takahashi, H.; Yamamoto, H.; Nozaki, H. Journal of the American Chemical Society. (1973), 95(8), 2694-2695.
14. Hans, J.; Wallace, E.M.; Zhao, Q.; Lyssikatos, J.P.; Aicher, T.; Laird, E.; Robinson, J.; Allen, S. PCT Int. Appl. (2006), 202 pp. (S)

Figure 13e

IDENTIFICATION OF BACTERIAL AUTOINDUCER AND USE IN TREATING BACTERIAL PATHOGENICITY

This application claims benefit under 35 U.S.C. §119(e) of U.S. Provisional Ser. No. 60/976,587, filed Oct. 1, 2007 and U.S. Provisional Ser. No. 61/189,844, filed Aug. 22, 2008, which are herein incorporated in their entirety by reference.

GOVERNMENT INTERESTS

The invention was made with government support under grants from the National Institutes of Health, NIH 2R01 GM065859-05A1 and the National Science Foundation, NSF MCB-0639855 and with support from the HHMI. The government has certain rights in the invention.

BACKGROUND OF THE INVENTION

Bacterial communities track changes in their population densities by producing, releasing, and detecting diffusible signalling molecules called autoinducers. This process is called quorum sensing, as described in Miller, M. B. and Bassler, B. L. Quorum sensing in bacteria. *Annu. Rev. Microbiol.* 55, 165-199 (2001) and Waters, C. M. and Bassler, B. L. Quorum sensing: cell-to-cell communication in bacteria. *Annu. Rev. Cell Dev. Biol.* 21, 319-346 (2005), both of which are hereby incorporated by reference into this application. Population-wide responses of the bacteria to the accumulation of autoinducers shape group behaviors such as biofilm formation, virulence factor expression, bioluminescence, and sporulation, as described in Davies, D. G. et al. The involvement of cell-to-cell signals in the development of a bacterial biofilm. *Science* 280, 295-298 (1998); Passador, L., Cook, J. M., Gambello, M. J., Rust, L., and Iglewski, B. H. Expression of *Pseudomonas aeruginosa* virulence genes requires cell-to-cell communication. *Science* 260, 1127-1130 (1993); Eberhard, A. et al. Structural identification of autoinducer of *Photobacterium fischeri* luciferase. *Biochemistry* 20, 2444-2449 (1981); and Solomon, J. M., Lazazzera, B. A., and Grossman, A. D. Purification and characterization of an extracellular peptide factor that affects two different developmental pathways in *Bacillus subtilis*. *Genes Dev.* 10, 2014-2024 (1996), all of which are hereby incorporated by reference into this application. *Vibrio cholerae* bacteria use two parallel quorum-sensing systems (FIG. 1) to assess population density, as described in Miller, M. B., Skorupski, K., Lenz, D. H., Taylor, R. K., and Bassler, B. L. Parallel quorum sensing systems converge to regulate virulence in *Vibrio cholerae*. *Cell* 110, 303-314 (2002), both of which are hereby incorporated by reference into this application. In one system, the CqsS receptor responds to a molecule called *Cholerae* Autoinducer-1 (CAI-1), which is produced by the enzyme CqsA. CqsS is the *Cholerae* quorum-sensing Sensor and CqsA is the *Cholerae* quorum-sensing Autoinducer-synthase enzyme. In the second system, the LuxPQ receptor complex responds to the autoinducer-2 (AI-2) molecule, made by the LuxS enzyme. These two autoinducers, CAI-1 and AI-2, function synergistically to control gene regulation. CAI-1 is produced by several *Vibrio* species, suggesting that it functions as an intra-genus signal whereas AI-2 is produced and detected by a wide variety of bacteria and is presumed to facilitate interspecies communication, as described in Henke, J. M. and Bassler, B. L. Three parallel quorum-sensing systems regulate gene expression in *Vibrio harveyi*. *J. Bacteriol.* 186, 6902-6914 (2004), and Xavier, K. B. and Bassler, B. L. LuxS quorum sensing: more than just a numbers game. *Curr. Opin. Microbiol.* 6, 191-197 (2003), both of which are hereby incorporated by reference into this application. AI-2 is a set of interconverting molecules all derived from the precursor (S)-4,5-dihydroxypentane-2,3-dione (DPD), as described in Schauder, S., Shokat, K., Surette, M. G., and Bassler, B. L. The LuxS family of bacterial autoinducers: biosynthesis of a novel quorum-sensing signal molecule. *Mol. Microbiol.* 41, 463-476 (2001) and Miller, S. T. et al. *Salmonella typhimurium* recognizes a chemically distinct form of the bacterial quorum-sensing signal AI-2. *Mol. Cell.* 15, 677-687 (2004), both of which are hereby incorporated by reference into this application. In the Vibrios, the active AI-2 moiety is the furanosylborate diester (2S,4S)-2-methyl-2,3,3,4-tetrahydroxytetrahydrofuran borate. CAI-1 has a much more dramatic influence on target gene expression than AI-2, and is therefore the major quorum-sensing signal in *V. cholerae*, as described in Miller et al. (2002).

The prevalence of cholera disease in developing nations and the rise of antibiotic resistant strains of *V. cholerae* is a recognized health problem, as described in Wang, L. H. et al. A bacterial cell-cell communication signal with cross-kingdom structural analogueues. *Mol. Microbiol.* 51, 903-912 (2004), hereby incorporated by reference into this application. On a broader scale, a wide spectrum of bacterial diseases are known which require new therapeutic strategies as bacteria develop antibiotic resistance. It would be beneficial if, rather than searching for new antibiotics, a new therapeutic strategy were to be formulated for these bacterial diseases. On a still broader scale, bacterial pathogens infect animals and there is a need to control these animal diseases. For example, *Vibrio harveyi* and closely related species are pathogens of shrimp, molluscs and fish. There is a strong need to develop compounds and strategies to control pathogens of food animals such as those in the aquaculture industry. Thus, on the broad scale, there is a need to develop strategies to manipulate quorum-sensing-controlled processes in bacteria.

SUMMARY OF THE INVENTION

In one aspect, the invention provides an isolated compound that has autoinducer activity in bacteria, wherein the compound is an α-hydroxyketone having a CH3CH2CH(OH)— unit bonded to an unbranched alkyl chain. In a preferred embodiment the compound contains from eight to thirteen carbons.

In another aspect, the invention provides a compound having the capability to function as a bacterial autoinducer in the CAI-1 quorum sensing pathway. The compound is (S)-3-hydroxytridecan-4-one or an analogue. In one embodiment, the invention provides a composition comprising the compound, wherein the composition inhibits virulence in *V. cholerae*. The invention further relates to use of the composition in the manufacture of a medicament for treating cholera. In another embodiment, the invention provides a composition comprising the compound, wherein the composition inhibits biofilm formation.

In a related aspect, the invention relates to a method of inhibiting quorum-sensing dependent activity in *Vibrio* spp. comprising contacting the *Vibrio* bacteria with an effective amount of the compound. In various embodiments, the quorum-sensing dependent activity is biofilm formation or pathogenicity. In a preferred embodiment, the pathogenicity is caused by production of a virulence factor. In a particularly preferred embodiment, the virulence factor is toxin co-regulated pilus (TCP). In an alternative embodiment, the method is for treating cholera comprising contacting *V. cholerae* bacteria with the compound. In a preferred embodiment, the invention relates to a method for repressing *V. cholerae* pathogenicity comprising contacting *V. cholerae* bacteria with the compound and with (S)-4,5-dihydroxypentane-2,3-dione (DPD).

In another aspect, the invention relates to a method of preparing an α-hydroxyketone compound having a CH3CH2CH(OH)— unit bonded to a long unbranched alkyl chain comprising (1) introducing a cqsA gene into *Escherichia coli*, (2) culturing the *E. coli* in bacterial culture medium, (3) removing the *E. coli* from the bacterial culture medium after culturing to produce a cell-free bacterial culture medium and (4) purifying a fraction having CAI-1 activity from the cell-free bacterial culture medium.

In preferred embodiments of the above aspects, the bacteria are *Vibrio* spp. and in a particularly preferred embodiment the bacteria are *V. cholerae*. In other preferred embodiments the compound is the S or R stereoisomer of 3-hydroxytridecan-4-one or is an analogue wherein the analogue differs in the long unbranched alkyl chain by having a C9-acyl or C8-acyl unit in place of the C10-acyl unit of 3-hydroxytridecan-4-one. In a particularly preferred embodiment, the compound is (S)-3-hydroxytridecan-4-one. In another embodiment, the compound is an analogue of (S)-3-hydroxytridecan-4-one.

BRIEF DESCRIPTION OF THE FIGURES

FIG. 5. Signalling Molecule Reference. a, Sampling of autoinducers used by a limited range of organisms. b, α-hydroxyketone insect pheromones resemble CAI-1.

(M+) and m/z 127 (C8-acyl) support assignment as 3-hydroxyundecan-4-one (C11). c, MS fragmentation of major component 5 (12.6 min). m/z 214 (M+) and m/z 155 (C10-acyl) support assignment as 3-hydroxytridecan-4-one (C13).

Figure 7:
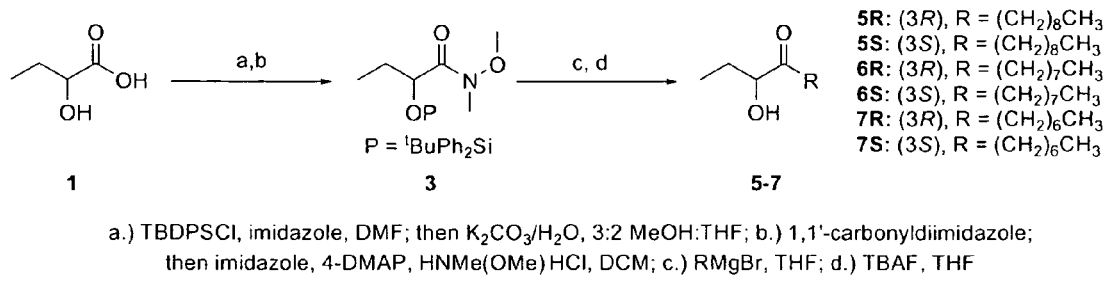
FIG. 7. Asymmetric Synthesis of CAI-1. The synthesis methods of the compounds illustrated in the figure are described in detail in Example 2.
Figure 8:
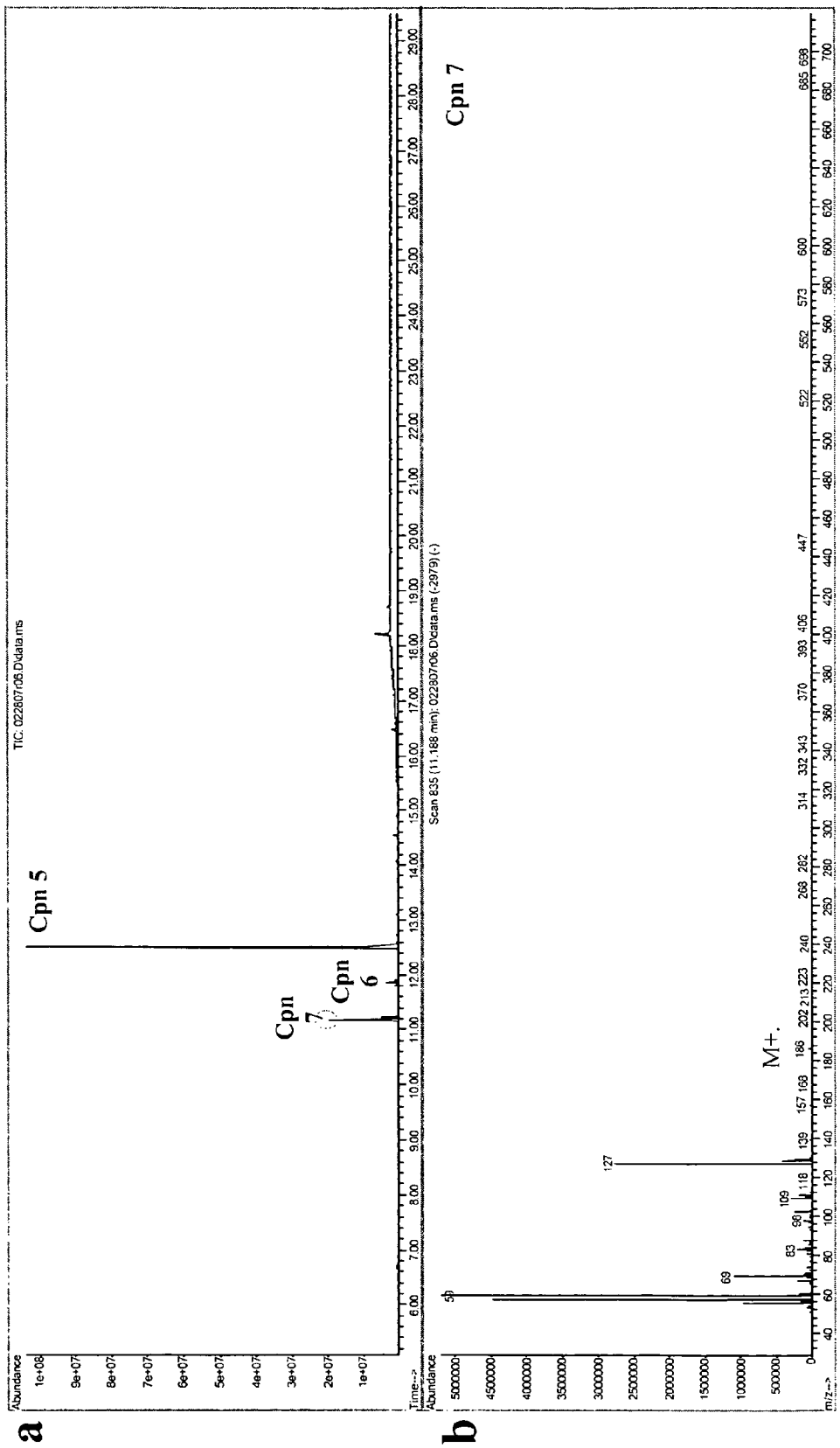
FIG. 8. GC/MS Analysis of *E. coli* Active Extract. a, GC/MS trace of HPLC-purified active extract from *E. coli*. Minor component compounds 7 (11.2 min) and 6 (11.9 min) and major component compound 5 (12.6 min) are shown. Refer to FIG. 7 for numerical assignments for compounds. See Example 1 for HPLC conditions. GC/MS conditions: Injection: 1.0 μL, He carrier gas. Heating sequence: 5 min at 50° C., then 20° C./min increase to 300° C. and hold for 12 min. Total time: 29.50 min. Scan range: 50-700 m/z. b, MS fragmentation of minor component 7 (11.2 min). m/z 186
Figure 8:
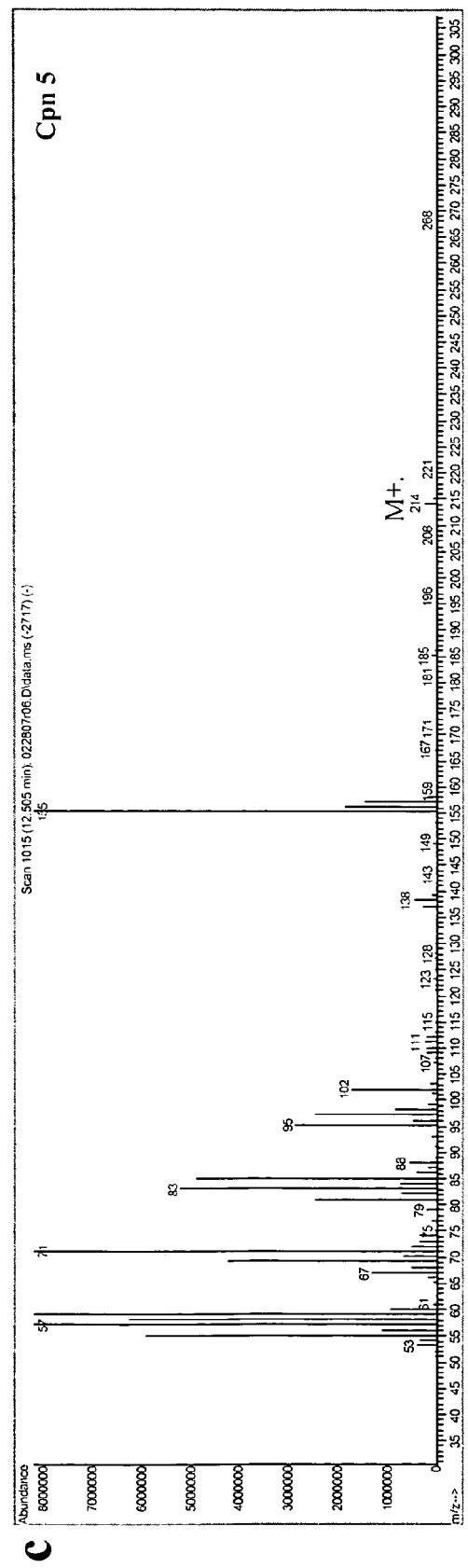
Figure 9:
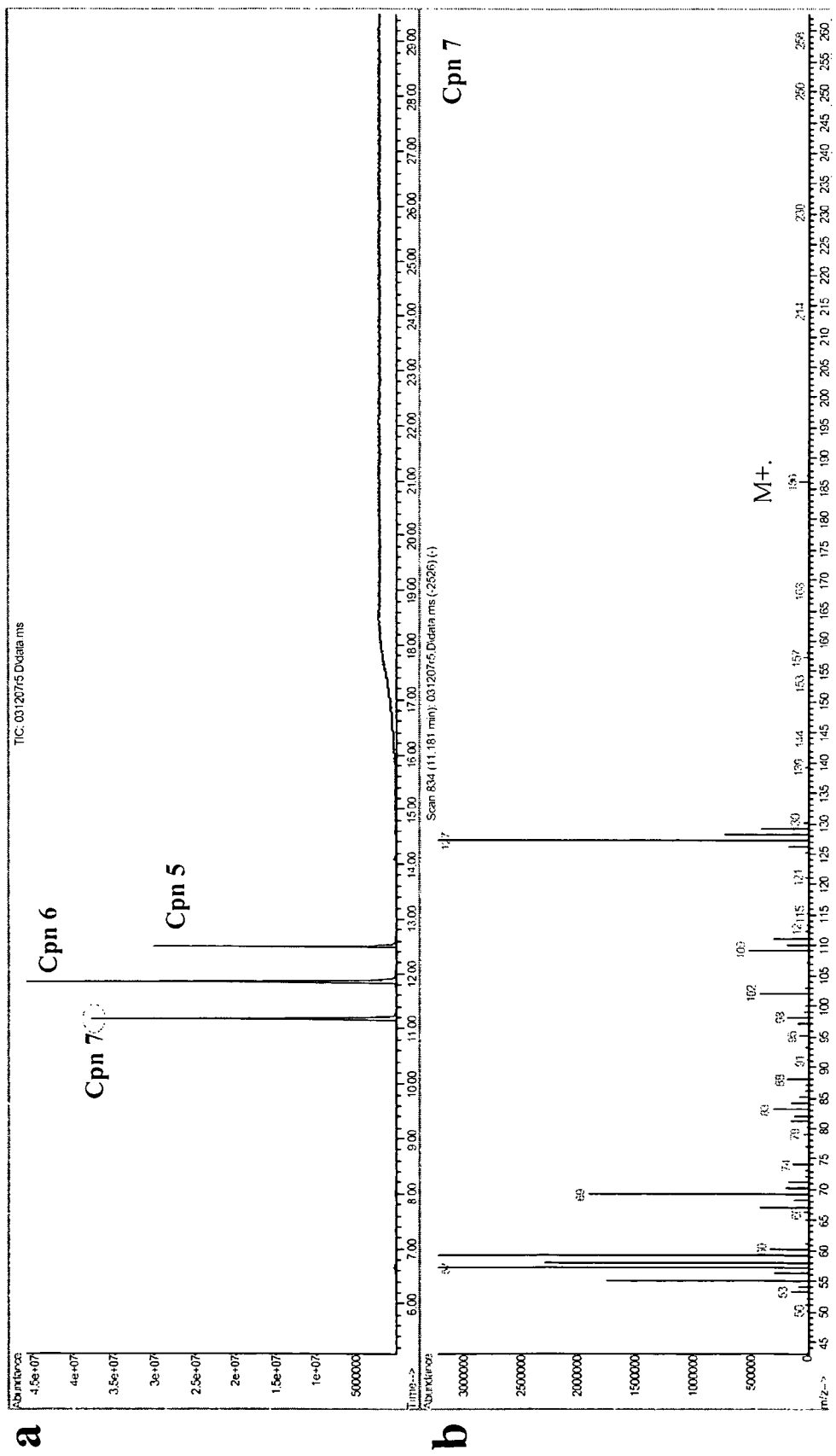
Figure 9:
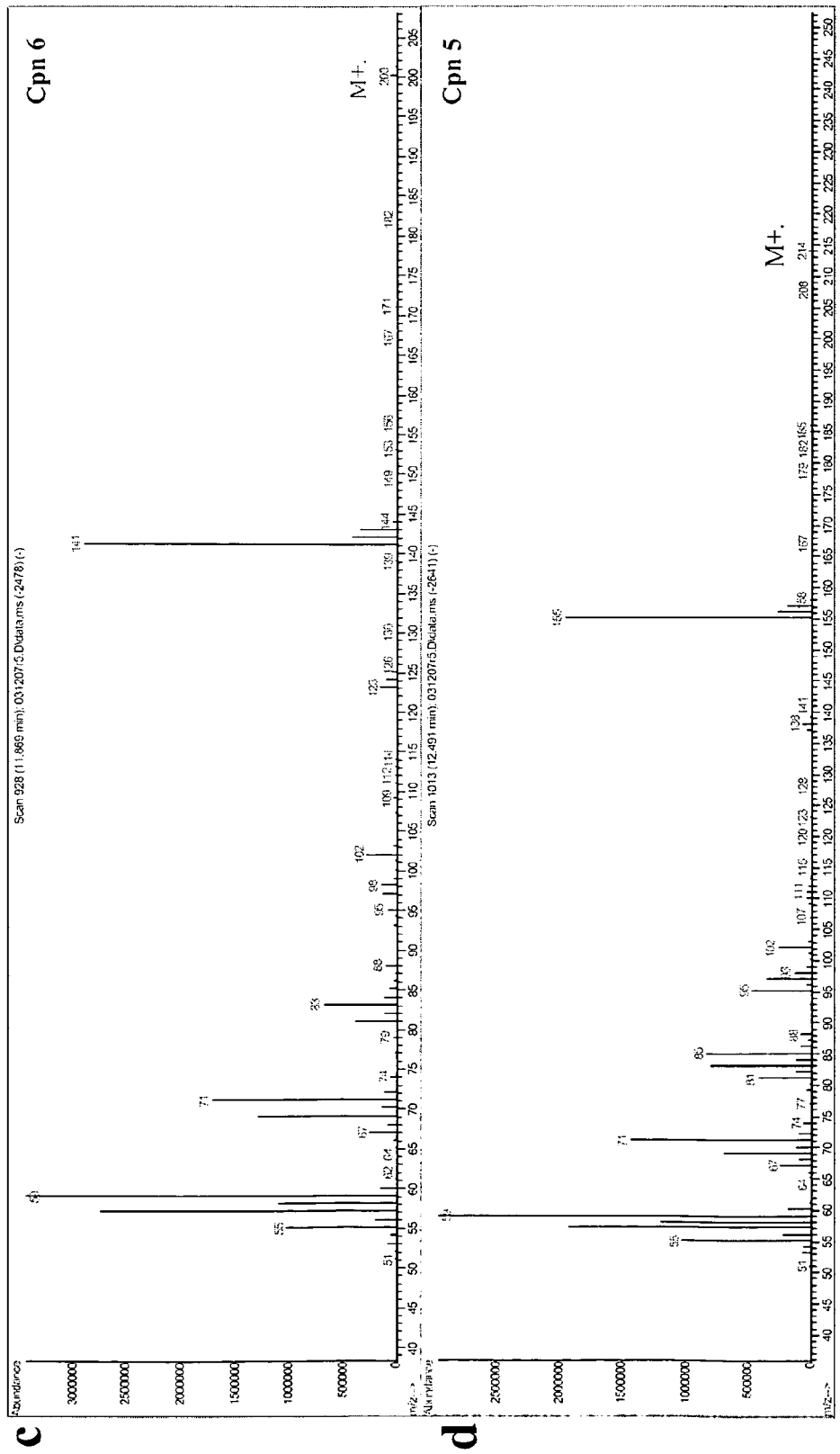

FIG. 9. GC/MS Analysis of Synthetic Standards. a, GC/MS trace of ~1:1:1 mixture of compounds 7 (11.2 min), 6 (11.9 min), and 5 (12.6 min), (3-hydroxyundecan-4-one (C11), 3-hydroxydodecan-4-one (C12), and 3-hydroxytridecan-4-one (C13), respectively), each individually obtained though chemical synthesis (see FIG. 7). See Legend 8a for GC/MS conditions. b, MS fragmentation of synthetic C11 compound 7 (11.2 min). m/z 186 (M+) and m/z 127 (C8-acyl) are characteristic of this molecule. Note match to elution time and fragmentation of component 7 in FIG. 8a. b. c, MS fragmentation of synthetic C12 compound 6 (11.9 min). m/z 200 (M+) and m/z 141 (C9-acyl) are characteristic of this molecule. Note match to elution time of component 6 in FIG. 8a. d, MS fragmentation of synthetic C13 compound 5 (12.6 min). m/z 214 (M+) and m/z 155 (C10-acyl) are characteristic of this molecule. Note match to elution time and fragmentation of major component 5 in FIG. 8a, c (E. coli) and in FIG. 10 (V. cholerae).

Figure 10:
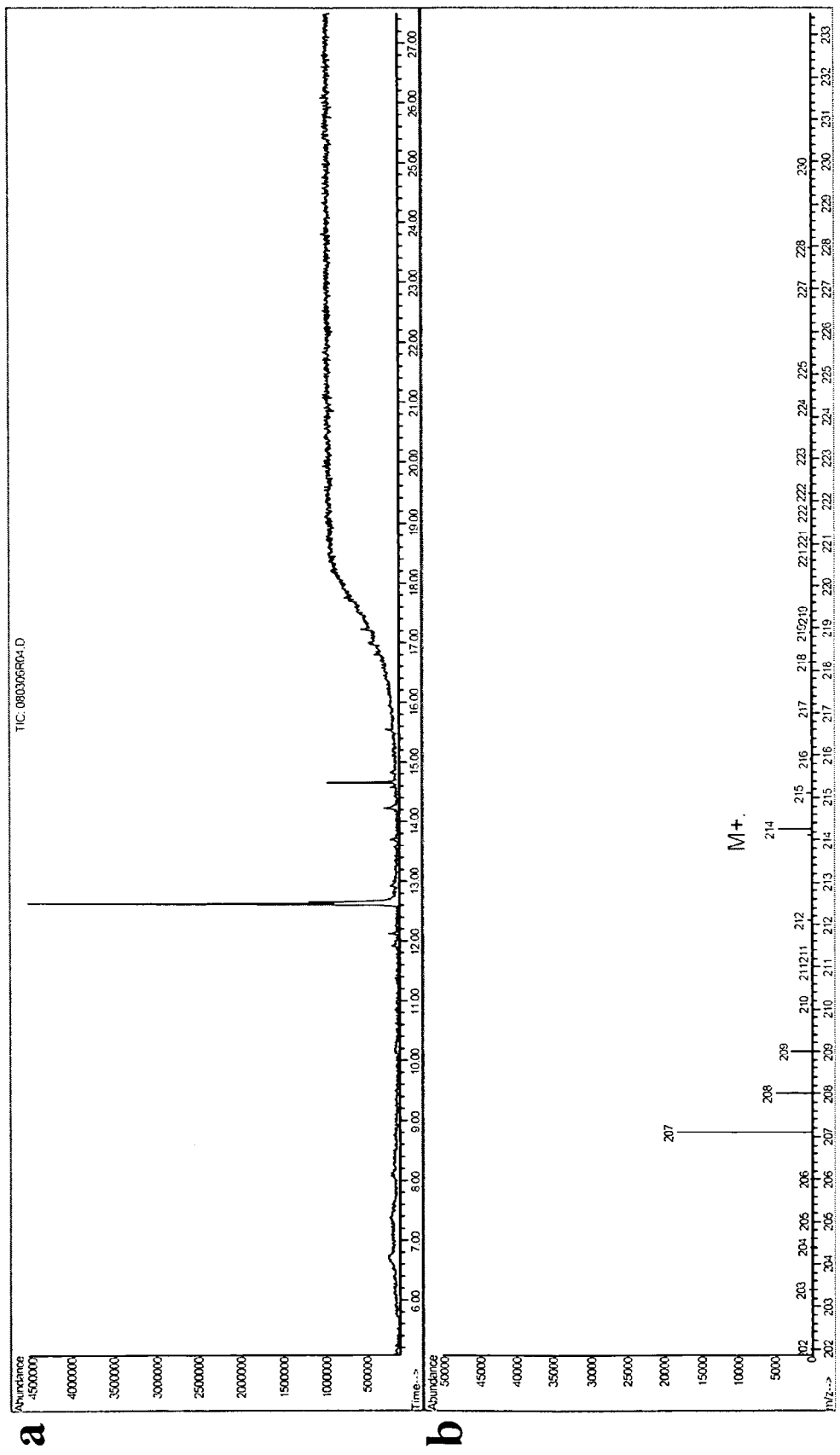
Figure 10:
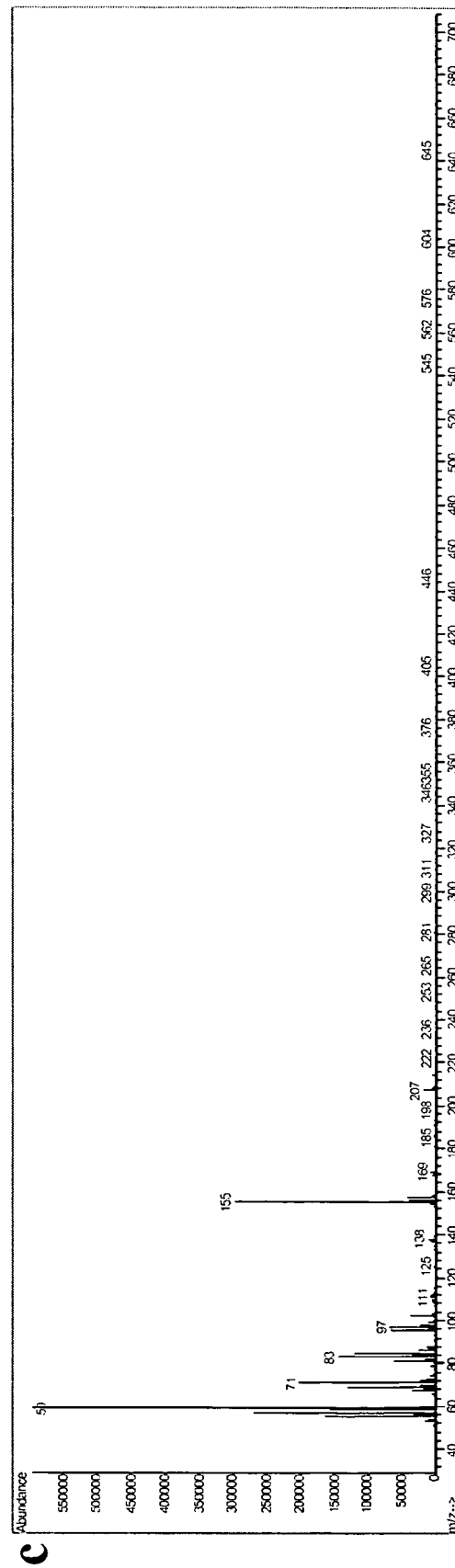

FIG. 10. GC/MS Analysis of V. cholerae Active Extract. a, GC/MS trace of HPLC-purified active extract from V. cholerae. The dominant component of interest is circled. Elution time of 12.6 matches that for the major component 5 from the E. coli extract (FIG. 8a) and synthetic 3-hydroxytridecan-4-one (C13 cpn 5, FIG. 9a). See Example 1 for HPLC conditions. See FIG. 8a for GC/MS conditions. b, Enlarged M+ region of MS fragmentation of major component. m/z 214 (M+) supports assignment as 3-hydroxytridecan-4-one (C13 compound 5). See also FIG. 9d. c, MS fragmentation of major component. m/z 155 (C10-acyl) supports assignment as 3-hydroxytridecan-4-one (C13 compound 5). See also FIG. 9d.

Figure 11:
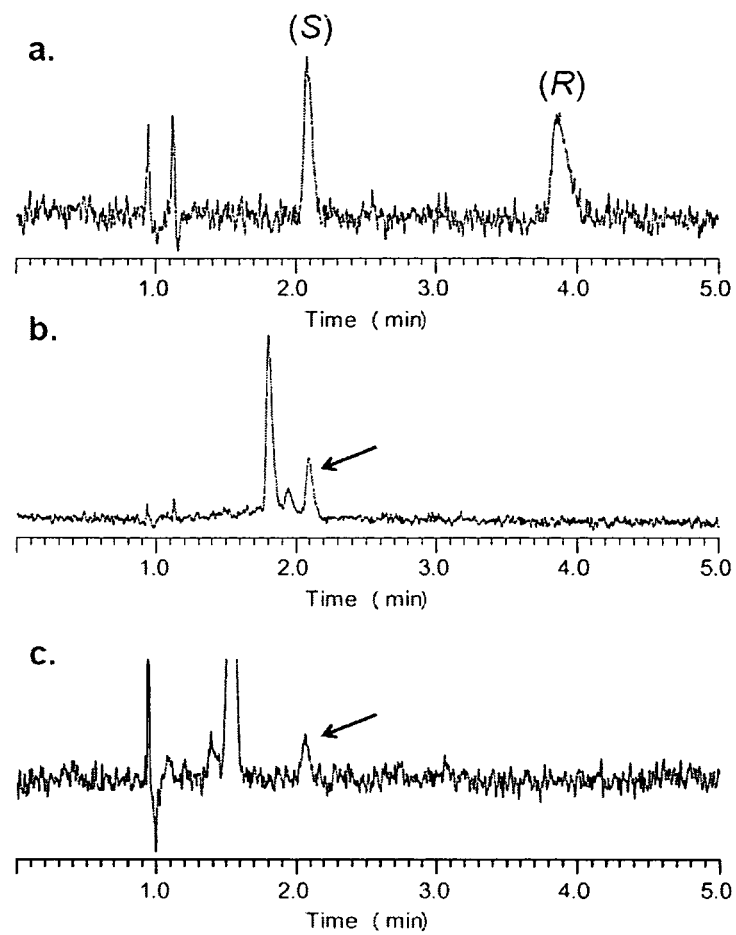

FIG. 11. Determination of CAI-1 Stereochemistry. a, Chiral SFC trace of ~1:1 mixture of (S)-CAI-1 and (R)-CAI-1, each individually obtained through asymmetric chemical synthesis (see FIG. 7). (S) elutes at 2.1 min.; (R) elutes at 3.9 min. Conditions: Chiralpak AD-H, 15% MeOH/CO$_2$ (100 bar), 3 mL/min, 280 nm. b, Chiral SFC trace of HPLC-purified active extract from E. coli, estimated at ~90% purity by $^1$H NMR analysis (see Example 1, FIG. 2, FIG. 8). Arrow indicates the elution of (S)-CAI-1. No (R)-CAI-1 is present. Conditions as in a. c, Chiral SFC trace of HPLC-purified active extract from V. cholerae (see Example 1 and FIG. 10). Arrow indicates the elution of (S)-CAI-1. No (R)-CAI-1 is present. Conditions as in a.

Figure 12:
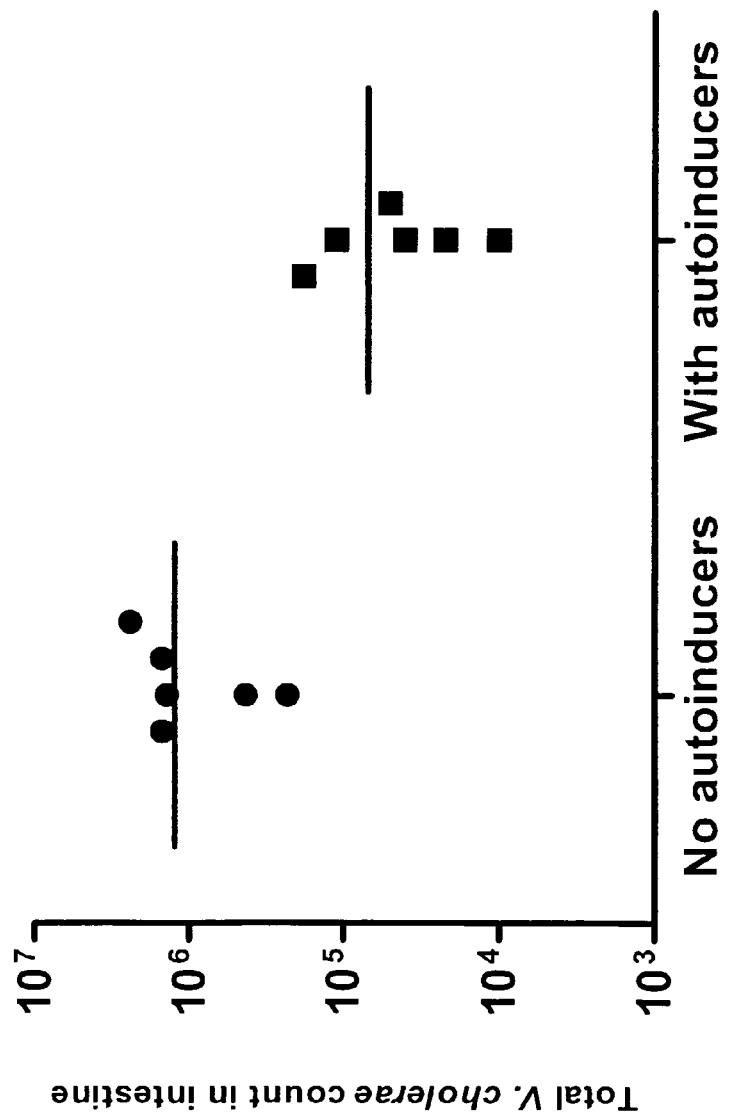

FIG. 12. Effect of Autoinducers on the Colonization of V. cholerae in an Infant Mouse Model. CD1 infant mice were infected orally with V. cholerae. Seven hours post-infection the mice were sacrificed and the number of bacteria in the intestine was determined by plating intestinal homogenate on selective medium. The experimental group received V. cholerae that had been cultured 30 minutes with synthetic autoinducers and the mice were additionally administered the autoinducers orally at two and five hours post-infection. Control mice were infected with non-autoinducer-treated V. cholerae and the solutions administered at two and five hours omitted autoinducer.

Figure 13D:
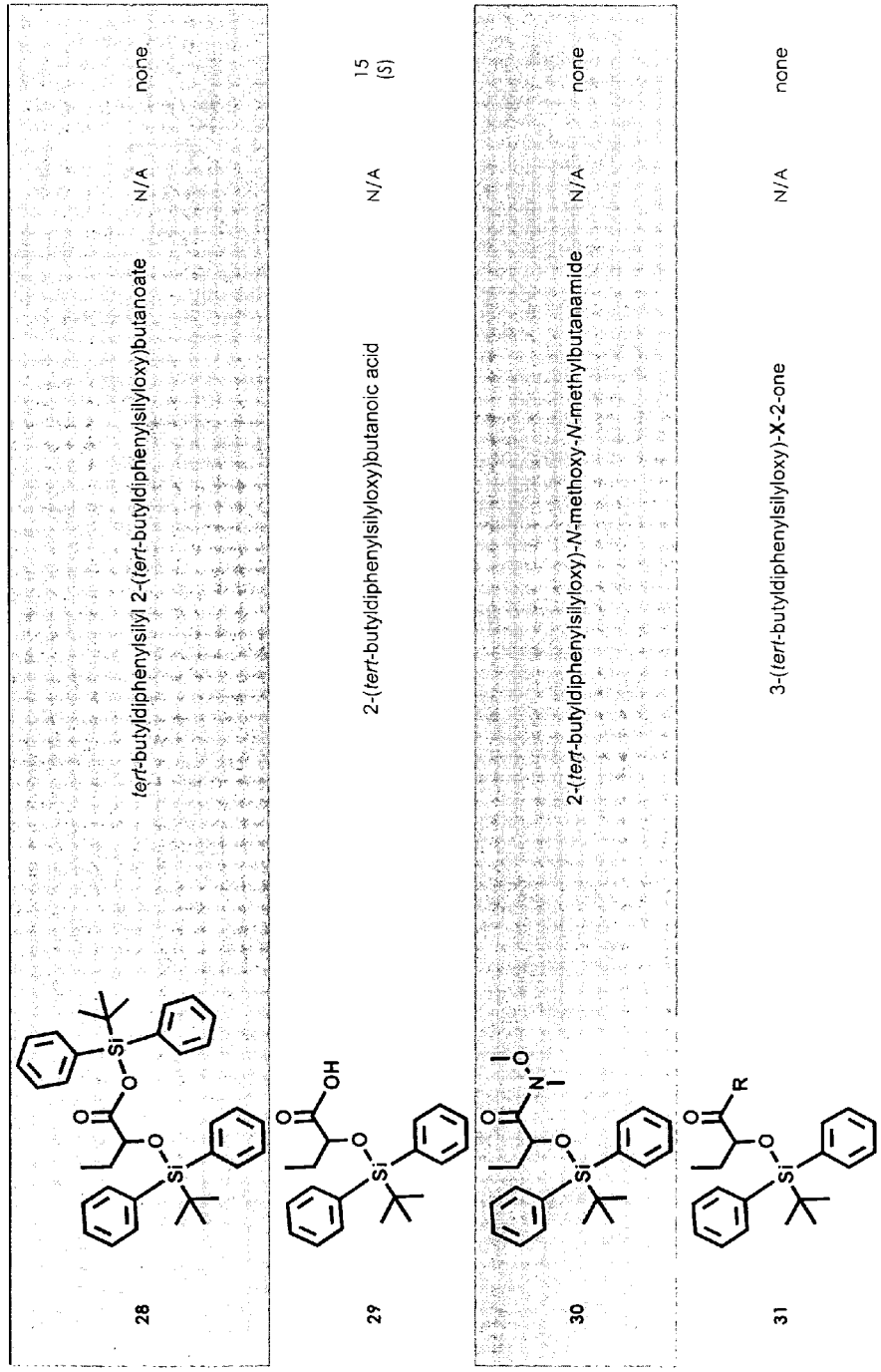

FIG. 13. CAI-1 Analogues. The natural CAI-1 was used as a reference compound for CAI-1 activity, determined by the measurement of bioluminescence in a CAI-1 reporter strain MM920. Analogues were substituted for CAI-1 in the bacterial culture medium and comparative measurements of bioluminescence were made.

DETAILED DESCRIPTION OF THE INVENTION

At low cell density, in the absence of autoinducers, V. cholerae expresses virulence factors and forms biofilms, as described in Miller et al. (2002), Hammer, B. K. and Bassler, B. L. Quorum sensing controls biofilm formation in Vibrio cholerae. Mol. Microbiol. 50, 101-104 (2003), and Zhu, J. and Mekalanos, J. J. Quorum sensing-dependent biofilms enhance colonization in Vibrio cholerae. Dev. Cell 5, 647-656 (2003), all of which are hereby incorporated by reference into this application. This pattern of gene expression enables host colonization and contributes to persistence in the environment. In the presence of autoinducers, at high cell density, quorum sensing represses both virulence factor expression and bio film formation. These events are proposed to allow V. cholerae to exit the host, re-enter the environment in large numbers, and initiate a new cycle of infection.

Structural identification of CAI-1 shows that it is an α-hydroxyketone and, thus, a new type of autoinducer. A standard activity curve was developed using synthetic CAI-1 that allowed the autoinducer concentration in high cell density V. cholerae cell-free culture fluids to be estimated as being 1.25 µM (data not shown). This is well in line with the concentrations and signalling activities of other bacterial autoinducers, which range from low micromolar (homoserine lactones) to nanomolar (AI-2), as described in Eberhard et al. (1981) and Neiditch, M. B. et al. Ligand-induced asymmetry in histidine sensor kinase complex regulates quorum sensing. Cell 126, 1095-1108 (2006), hereby incorporated by reference into this application.

Figure 1:
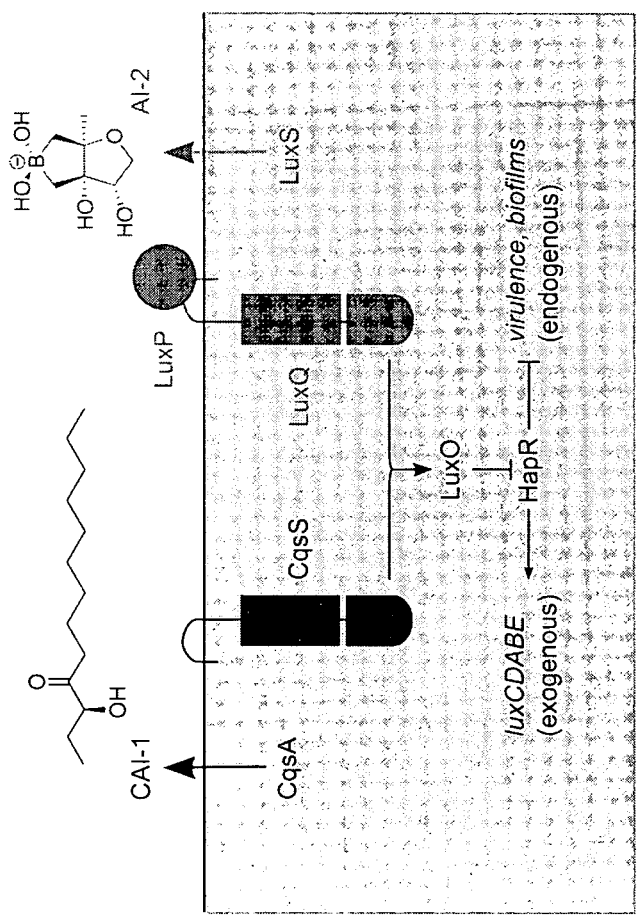
FIG. 1. Simplified Model for *V. cholerae* Quorum Sensing. The autoinducers CAI-1 ((S)-3-hydroxytridecan-4-one) and AI-2 ((2S,4S)-2-methyl-2,3,3,4-tetrahydroxytetrahydrofuran borate) are produced by the synthases CqsA and LuxS, as described in Miller et al. (2002) and Chen, X. et al. Structural identification of a bacterial quorum-sensing signal containing boron. *Nature* 415, 545-549 (2002), respectively, hereby incorporated by reference into this application. CAI-1 is detected by the CqsS receptor, and two proteins, LuxP and LuxQ, function together to detect AI-2. Information from both autoinducers is transduced through the LuxO protein to control the levels of the master transcription factor HapR. At low cell density, in the absence of autoinducers, HapR is not produced, so virulence factors are expressed and bio films are formed. However, no light from a luciferase (luxCDABE) cassette is produced. At high cell density, in the presence of autoinducers, LuxO is inactivated, HapR is produced, and it represses genes for virulence factor production and bio film formation while activating expression of the luxCDABE genes, resulting in bioluminescence. The complete circuit is reported in Hammer and Bassler, and as described in Colnaghi Simionato, A. V., da Silva, D. S., Lambais, M. R., and Carrilho, E. Characterization of a putative *Xylella fastidiosa* diffusible signal factor by HRGC-EI-MS. *J. Mass Spectrom.* 42, 490-496 (2007), all of which are hereby incorporated by reference into this application.

The "activity" of CAI-1 refers to the ability to activate the CAI-1 quorum-sensing circuit (FIG. 1). In bacteria, the activity involves the initial interaction between CAI-1 and the sensor molecule CqsS, with the extracellular signalling information being transduced through LuxO and HapR to control measurable activities or biomarkers of the bacteria (e.g., virulence, bio film formation, host colonization, bioluminescence). As used herein, "quorum-sensing activity", "biological activity", "autoinducer activity", "CAI-1 activity" and similar terms refer to the ability to activate the quorum-sensing circuit, which may be measurable as various quorum-sensing regulated traits, e.g., virulence, host colonization, biofilm formation, etc. As described herein, a V. cholerae reporter strain was used to provide quorum-sensing dependent bioluminescence as a measure of the quorum-sensing activity of the molecules under study.

Because autoinducers terminate rather than promote virulence in V. cholerae, activation of quorum sensing in V. cholerae by providing autoinducer forms the basis of a novel strategy for therapeutic intervention in bacterial pathogenicity. The major V. cholerae autoinducer, CAI-1, was identified, characterized, and synthesized, and the autoinducer was used to control quorum-sensing-regulated traits. CAI-1 represses production of the virulence factor component, toxin co-regulated pilus (TCP). CAI-1 inhibits bio film formation. Furthermore, CAI-1 acts therapeutically to reduce the ability of V. cholerae to colonize its host.

TcpA is a subunit of the virulence factor TCP. TCP immunoblots showed that CAI-1 is capable of blocking virulence factor expression, and V. cholerae mutants 'locked' at high cell density are completely avirulent, as described in Miller et al. (2002) and Zhu, J. et al. Quorum-sensing regulators control virulence gene expression in Vibrio cholerae. Proc. Natl. Acad. Sci. USA 99, 3129-3134 (2002), hereby incorporated by reference into this application. This is noteworthy given the prevalence of cholera in the developing world and the rise of antibiotic resistant strains of V. cholerae, as described in Wang et al. (2004). That the autoinducer itself, and not an autoinducer antagonist, is an inhibitor of pathogenicity factors is a peculiarity of the V. cholerae disease process. Most pathogenic bacteria mount a long-lasting persistent infection and, in cases in which quorum sensing is involved, the accumulation of autoinducers at high-cell density promotes virulence factor expression, as described in Passador, L., Cook, J. M., Gambello, M. J., Rust, L., and Iglewski, B. H. Expression of *Pseudomonas aeruginosa* virulence genes requires cell-to-cell communication. Science 260, 1127-1130 (1993), hereby incorporated by reference into this application. *V. cholerae*, by contrast, elicits a self-limiting disease. At high-cell density, the bacteria are flushed from the host back into the environment. Consistent with this, autoinducer accumulation terminates virulence factor expression. This reciprocal relationship between autoinducer concentration and virulence in *V. cholerae* provides a unique opportunity to exploit quorum sensing to control pathogenicity. Moreover, the simplicity and inherent stability of CAI-1 may prove to be principal virtues in the development of applications for bacterial control (see FIG. 6). Thus, interference with quorum-sensing processes in general (either pro- or anti-) has tremendous promise in the clinical setting for control of bacterial pathogenicity.

In accord with these findings, the invention provides the *V. cholerae* CAI-1, which is structurally identified as (S)-3-hydroxytridecan-4-one, and analogues of this compound. In various embodiments, the compound or analogues are substantially purified to 75%-89% purity, more preferably to 90%-99% purity, or more preferably to greater than 99% purity. With respect to these compounds, pharmaceutical compositions are provided containing CAI-1 or CAI-1 analogue as therapy for cholera.

The pharmaceutical compositions can be administered by any mode known in the art. Representative modes of administration are oral, nasal, topical (including buccal and sublingual) or parenteral administration. Oral administration is a preferred mode of administration. Fluid dosage forms can allow for rehydration along with therapy. Solid dosage forms for oral administration can include, for example, capsules, tablets, pills, powders, tinctures and granules. The solid dosage forms can be an admixture with food and chewable forms. In such solid dosage forms, the active compound is admixed with at least one inert pharmaceutically acceptable carrier such as sucrose, lactose, or starch. In the case of capsules, tablets and pills, the dosage forms can also comprise buffering agents. The solid dosage forms can additionally be prepared with enteric coatings. A skilled artisan can determine which form of administration is best in a particular case for balancing the dose needed versus periodic delivery.

A therapeutically effective amount of the active ingredient will be determined dependent upon recognized variables such as age and weight of the subject; the particular route of administration and the particular condition of the subject. The suitability of treatment schedules and the aforementioned modes of administration are determined by those of skill in the art, using routine procedures. For example, those of skill in the art will be able to take the information disclosed in this specification and optimize treatment regimes for human subjects in accordance with the specification.

The compositions (and thus the methods) of the invention can be used alone or in conjunction with other therapies including, for example, administration of other therapeutic agents (including rehydrating solutions).

It will be appreciated that the treatment methods of the invention are useful in the fields of human medicine and animal treatment. Thus, the subject or individual to be treated may be a mammal, preferably human, or other animals, such as fish and marine animals. In the treatment of animals in an aquaculture environment, the active therapeutic may be added to foodstuffs or media. *V. harveyi, V. parahaemolyticus*, and *V. campbellii* are representative of bacterial pathogens of fish and shrimp. However, the invention is not limited by mention of these representative species.

The biological activity of CAI-1 is sensitive to side chain length, as the thirteen-carbon molecule has 8-fold greater activity than the twelve-carbon molecule, which likewise, is 8-fold more active than the eleven-carbon molecule (FIG. 3). The configuration of the hydroxyl group is also important, albeit to a lesser extent (roughly 2-fold differences). The relatively small effect of the configuration of the C3 hydroxyl on activity is surprising, given that there are only two functional groups (hydroxyl and carbonyl) on the molecules. The limits of and requirements for CAI-1 recognition by the CqsS receptor were made apparent through the synthesis of related molecules, with a particular focus on functional groups and stereochemistry at the C3 and C4 positions as well as backbone length (Examples 1, 2, 8).

Analogues of (S)-3-hydroxytridecan-4-one (CAI-1) were synthesized and demonstrated control over quorum-sensing-regulated traits. The term "analogue" is meant to include a molecule that is structurally similar to the parent molecule (CAI-1), but different in that chemical groups have been substituted, added, or removed so as to make the analogue structurally distinct from the parent compound.

The analogue may possess additional or lack certain of the quorum sensing activity of the parent molecule. Such analogues may be naturally occurring or synthetic. Representative of simple substitution analogues are substitution of (═O) for (—OH) or vice versa; substitution of chiral alternatives or chiral mixture; substitution with $—NH_3Cl$, —Cl, —Br, —SH, phenyl, methyl, tent-butyl or ($-D_2$). Representative analogues also include those obtained by lengthening or shortening the number of hydrocarbons in the alkyl chain or removing a functional group. The examples provided herein are representative and are not meant to be limiting.

When CqsA was introduced into and expressed in *E. coli*, the bacteria released into the culture medium (S)-3-hydroxytridecan-4-one (thirteen carbons) with trace amounts of 3-hydroxydodecan-4-one (twelve carbons) and 3-hydroxyundecan-4-one (eleven carbons). (FIG. 1). In contrast, *V. cholerae* produces exclusively the 13-carbon S stereoisomer. These findings suggest that CqsA couples a standard 10-carbon fatty acyl unit with a three-carbon moiety to produce CAI-1 and that high-level production of CqsA in heterologous *E. coli* exhausts the supply of the 10-carbon acyl substrate enabling minor amounts of shorter fatty acyl chains (e.g., C8) to be incorporated into the molecule.

The biochemical mechanism underlying production of CAI-1 by CqsA was not previously known. However, database analysis shows that CqsA is similar to pyridoxal phosphate (PLP)-binding aminotransferases, of which 8-amino-7-oxononanoate synthetase (AONS) shares the most homology. Related PLP-dependent aminotransferases typically catalyze condensations between amino acids and carboxylic thioesters, but the repertoire of PLP-dependent enzymes is diverse, as described in Eliot, A. C. and Kirsch, J. F. Pyridoxal phosphate enzymes: mechanistic, structural, and evolutionary considerations. *Annu. Rev. Biochem.* 73, 383-415 (2004), hereby incorporated by reference into this application. None, however, is known to generate an α-hydroxyketone like CAI-1 or an α-diketone that could be a possible precursor to CAI-1. The finding that introduction of cqsA into *E. coli* is sufficient for autoinducer production suggested that, either CAI-1 is made from commonly occurring metabolic intermediates and only one enzyme (i.e., CqsA) is required, or alternatively, that *E. coli* provides the additional enzyme(s) needed to synthesize the molecule. In the case of the former, CqsA would be the first PLP-dependent aminotransferase to perform a generic coupling of carbon units to produce an α-hydroxyketone. In vitro studies are able to define the biosynthetic mechanism of CAI-1 production.

The two largest families of autoinducer signals, the homoserine lactones used by the Gram-negative bacteria and the oligopeptides used by Gram-positive bacteria, contain numerous related molecules, each possessing significant species specificity, as described in Taga, M. E. and Bassler, B. L. Chemical communication among bacteria. *Proc. Natl. Acad. Sci. USA* 100, 14549-14554 (2003), hereby incorporated by reference into this application. By contrast, AI-2 functions generically across species via spontaneous derivitization of a shared precursor, DPD, as described in Waters et al. (2005) and Xavier et al. (2003). Finally, there are particular autoinducer signals (and their corresponding synthases) that have unique structures and are produced by, and active only in, closely-related organisms, such as the quinolones (Pseudomonads), the γ-butyrolactones (Streptomycetes), 3-hydroxypalmitic acid methyl ester (*Ralstonia*), the diffusible signal factors (DSF; Xanthomonadaceae), and now the α-hydroxyketone CAI-1 (Vibrios) (see FIG. 5a for structures), as described in Pesci, E. C. et al. Quinolone signalling in the cell-to-cell communication system of *Pseudomonas aeruginosa*. Proc. Natl. Acad. Sci. USA 96, 11229-11234 (1999); Horinouchi, S, and Beppu, T. A-factor as a microbial hormone that controls cellular differentiation and secondary metabolism in *Streptomyces griseus*. Mol. Microbiol. 12, 859-864 (1994); Flavier, A. B., Clough, S. J., Schell, M. A., and Denny, T. P. Identification of 3-hydroxypalmitic acid methyl ester as a novel autoregulator controlling virulence in *Ralstonia solanacearum*. Mol. Microbiol. 26, 251-259 (1997); Wang et al. (2004); and Colnaghi Simionato et al. (2007), all of which are hereby incorporated by reference into this application. Due to their limited distribution, clues to their existence are not revealed by comparison of diverse genome sequences. Rather, each of these molecules was individually discovered based on a particular phenotype in a particular bacterium. Based on this, we propose the existence of additional potent quorum-sensing signals of unique structure and restricted ranges of target organisms.

Accordingly, another aspect of the invention provides that bacteria containing CqsA are capable of synthesizing a quorum-sensing signal like the α-hydroxyketone CAI-1. As representative of such bacteria, are *V. cholerae, V. parahaemolyticus, V. harveyi, V. alginolyticus, V. campbellii, V. spledidus, V. angustum, V. shilonii, Photobacterium profundum, Chlorobium ferrooxidans, C. phaeobacteroides, C. limicola, Nitrococcus mobilis, Prosthecochloris aestuarii, Burkholderia xenovorans, Polaromonas* sp. JS666, *Polaromonas naphthalenivorans, Legionella pneumophila,* and *Ralstonia eutropha*.

The molecule (S)-3-hydroxytridecan-4-one was previously unknown in biology. However, other α-hydroxyketones are known to play key roles in biological signalling systems. For example, the male coffee white stem borer *Xylotrechus quadripes* Chevrolat uses the α-hydroxyketone (S)-2-hydroxydecan-3-one as a sex pheromone, as described in Flavier et al. (1997). Interestingly, females are attracted specifically to the S isomer of this compound. Similar α-hydroxyketones are produced and used as pheromones by other insects (see FIG. 5b). The biosynthetic steps responsible for production of these insect pheromones have not been defined and cannot, therefore, be compared to steps in CAI-1 synthesis. The similarities between the molecules, however, raise the possibility that their syntheses as well as their roles in communication arose from a distant common ancestor.

The molecule (S)-3-hydroxytridecan-4-one is identified as the natural CAI-1 autoinducer in *Vibrio cholerae*. It has now been determined that analogues of this molecule also have quorum sensing activity (See FIG. 13). Among the analogues contemplated in the present invention are the set of molecules whose structure is identified as $CH_3CH_2CH(R)C(=O)CH_2CH_2CH_2CH_2CH_2CH_2CH_2CH_2CH_3$, where R=—NH$_3$Cl, —(S)—NH$_3$Cl, —(R)—NH$_3$Cl, —Cl, —Br, or —SH. As representative, the analogue 3-(chloroamino)tridecan-4-one, when tested, exhibited equivalent activity to CAI-1. Also among the analogues contemplated are the set of molecules $CH_3CD_2CH(R)C(=O)CH_2CH_2CH_2CH_2CH_2 CH_2CH_2 CH_2CH_3$, where R=—OH or —NH$_3$Cl. As representative, the analogue 2,2-D$_2$-3-hydroxytridecan-4-one, when tested, exhibited equivalent activity to CAI-1. Also among the analogues contemplated are the set of linear hydrocarbons X carbons in length bearing a hydroxyl substituent at carbon 3 and a ketone substituent at carbon 4, where X=7, 9, 15, or 17. The analogues contemplated also include the set of linear hydrocarbons Y carbons in length bearing an (S)-hydroxyl substituent at carbon 3 and a ketone substituent at carbon 4, where Y=11, 12, or 13. This set includes the natural CAI-1, which of course exhibits 100% activity. Also among the analogues contemplated are the set of linear hydrocarbons Z carbons in length bearing an (R)-hydroxyl substituent at carbon 3 and a ketone substituent at carbon 4, where Z=11, 12, or 13. As representative, the analogue (R)-3-hydroxytridecan-4-one, when tested, exhibited forty percent of the activity of CAI-1. Among the analogues contemplated are the set of molecules $CH_3CH_2CH(R)CH(R')CH_2CH_2 CH_2CH_2 CH_2 CH_2CH_2CH_2CH_3$, where {R,R'}={=O, =O}, {—OH, —OH}, {=O, —OH}, {—H, =O}, {—OH, —H}, {=O, —H}, or {H, —OH}. As representative, the analogue tridecan-3,4-dione, when tested, exhibited 10 percent of the activity of CAI-1. Also among the analogues contemplated are the set of molecules $RCH(OH)C(=O)CH_2CH_2CH_2 CH_2 CH_2CH_2CH_2CH_3$, where R=methyl, tent-butyl or phenyl.

There now follow particular examples provided for the purpose of illustrating the invention and not be construed as limiting.

EXAMPLE 1

Purification and Identification of CAI-1

CAI-1 Purification. Autoinducer was purified from cell-free culture fluids of *E. coli* DH5α harboring inducible *V. cholerae* cqsA (VCA0523) on pTrc99A or from *V. cholerae* KSK1052 (El Tor C6706str ΔluxS) as specified. Expression of cqsA in *E. coli* was induced with IPTG. Following centrifugation and filtration, cell-free culture fluid was extracted with dichloromethane (DCM), evaporated, and assayed for CAI-1 activity using the bioluminescence assay described below. Following crude silica gel purification, concentrated extract (in DCM) was injected onto a (2×25-cm) ethyl-pyridine HPLC column and eluted using a gradient of increasing ethyl acetate in hexanes. Fractions were assayed for CAI-1 activity as described below.

*V. cholerae* strain C6706 is an O1 El Tor isolate from Peru, the source being the Centers for Disease Control and Prevention (CDC), Atlanta, Ga., as described in Thelin, K H and Taylor, R K. Toxin-coregulated pilus, but not mannose-sensitive hemagglutinin, is required for colonization by *Vibrio cholerae* O1 El Tor biotype and O139 strains. *Infection and Immunity* 64, 2853-2856 (1996), hereby incorporated by reference into this application.

CAI-1 Purification from *E. coli*. *V. cholerae* cqsA (VCA0523) was cloned into pTrc99A and transformed into *E. coli* strain DH5α. The recombinant strain was grown at room temperature with aeration in 2.4 L of M9 medium supplemented with glucose (4 g/L), leucine (0.5 g/L), and ampicillin (0.1 g/L). cqsA expression was induced for 16 h with 0.5 mM IPTG. Following centrifugation at 10,000×g and passage through a 0.22 μm filter, the cell-free culture fluid was mixed with 0.6 v dichloromethane (DCM) in a reparatory funnel. The organic phase was isolated, evaporated, and assayed for CAI-1 activity using the bioluminescent *V. cholerae* CAI-1 reporter strain MM920 (*V. cholerae* El Tor C6706str ΔcqsA ΔluxQ/pBB1 (luxCDABE from *V. harveyi*)), as described in Miller et al. (2002). The extract was dissolved in DCM and further purified by passage through silica gel with 0.5 L of 7:3 DCM:methanol, followed by concentration via evaporation. 50-100 mg of the concentrate was dissolved in ~1 mL DCM, injected onto a (2×25-cm) ethyl-pyridine HPLC column, and eluted using a gradient of increasing ethyl acetate in hexanes (0-80%) at 20 mL/min. Fractions were tested for CAI-1 activity; active fractions were pooled.

CAI-1 Purification from *V. cholerae*. KSK1052 (*V. cholerae* El Tor C6706str ΔluxS) was grown at 37° C. in 3-7 L of tryptone broth, with extraction and purification as in *E. coli* (above).

Chemical and Analytical Methods. $^1$H-NMR spectra were recorded using a Varian Unity (400 MHz), Varian Unity/INOVA (500 MHz), or a Bruker Avance II (500 MHz) spectrometer. Chemical shifts were calibrated according to a $CHCl_3$ internal standard.

$^{13}$C-NMR spectra were taken using a Varian Unity/INOVA (125.7 MHz); $^{13}$C-APT experiments were run on a Bruker Avance II (125.7 MHz) spectrometer. Chemical shifts for $^1$H and $^{13}$C NMR spectra were calibrated according to a $CHCl_3$ internal standard. Infrared spectra of samples dissolved in chloroform and analyzed in an NaCl cell were taken using a Nicolet 730 FT-IR spectrometer. Optical rotations were measured in chloroform using a PerkinElmer Model 341 polarimeter at 20° C. and 589 nm. EIMS analyses were performed at Princeton University. HRMS analysis was performed at Princeton University. Gas chromatography/mass spectroscopy analysis was conducted by the Scripps Research Institute Center for Mass Spectrometry, La Jolla, Calif.

Bioluminescence Assays. When assaying column fractions for autoinducer activity, 5% of each fraction was evaporated and dissolved in a mixture of water:acetonitrile (2:1). This preparation was added at 2% volume to the CAI-1 reporter strain MM920 (*V. cholerae* El Tor C6706str ΔcqsA ΔluxQ/pBB1 (luxCDABE from *V. harveyi*)) according to previously described methods, as described in Miller et al. (2002). Synthetic CAI-1 preparations were dissolved in DMSO and supplied at 0.5% total volume to MM920 at specified concentrations.

Figure 2A:
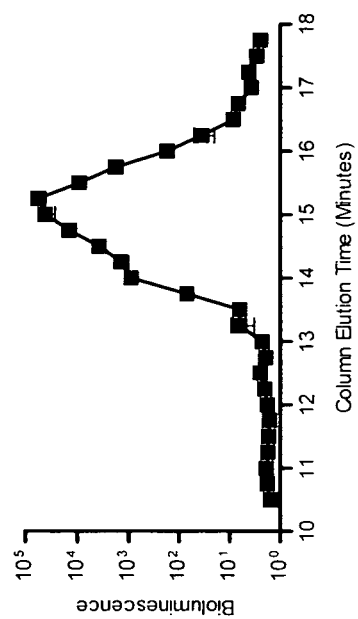
FIG. 2. Activity, $^1$H NMR Spectrum, and Structural Identification of CAI-1 as (S)-3-hydroxytridecan-4-one. a, CAI-1 was purified from cell-free extracts of *E. coli* pcqsA by HPLC separation. Activity, as measured by bioluminescence production from a CAI-1-responsive *V. cholerae* reporter strain, eluted as a single peak. Bioluminescence units are counts per second per 100 μL culture. Error bars represent standard deviations of triplicate samples. b, Active fractions were used for $^1$H NMR analysis. Chemical shift assignments are designated with lowercase letters. These NMR data, combined with data obtained from other analytical methods (see text and Example 1), were interpreted to assign CAI-1 the structure shown, 3-hydroxytridecan-4-one. Support for the S-isomer came from chiral chromatographic methods (FIG. 11).

Results. To purify and identify CAI-1, we introduced the cqsA gene (encoding the CAI-1 synthase, see FIG. 1) into *Escherichia coli*, which is sufficient for the production and release of high-level CAI-1 activity into culture fluids, as described in Miller et al. (2002) and Henke et al. (2004). Recombinant *E. coli* produces substantially more CAI-1 activity than does *V. cholerae* in minimal medium which simplified the initial purification and identification. CAI-1 activity was extracted from *E. coli* pcqsA cell-free culture fluids and purified via normal-phase HPLC. Activity was detected using a *V. cholerae* reporter strain engineered to express bioluminescence exclusively in response to exogenously provided CAI-1, as described in Miller et al. (2002). CAI-1 activity appeared as one peak following HPLC separation. Fractions in this peak contained 10.000-fold higher CAI-1 activity than did control samples (FIG. 2a).

Figure 2B:
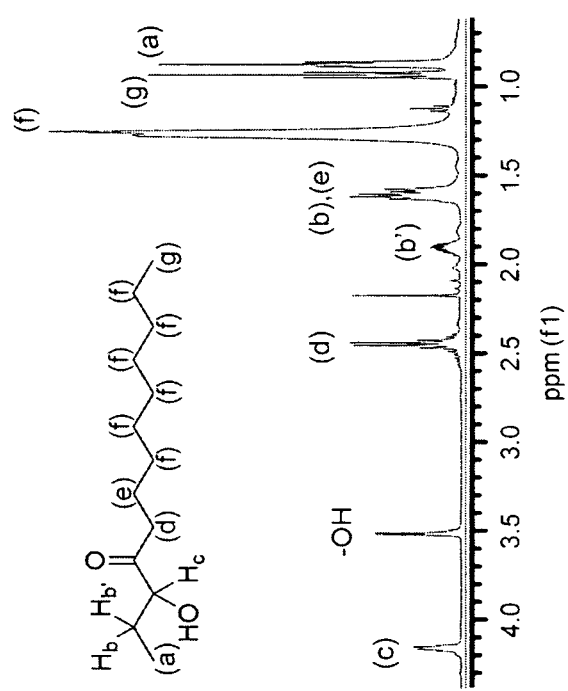

The structure of the dominant component (>90%) was assigned as the α-hydroxyketone shown in FIG. 2b based on spectroscopic evidence. A $D_2O$-exchangeable proton at δ 3.5 ppm and an IR absorbance at 3490 $cm^{-1}$ indicated the presence of a hydroxyl group. Using $^1$H double-quantum NMR spectroscopy, a correlation between the hydroxyl group and proton (c), together with correlations between protons (bb') and protons (a) and (c), respectively, established a $CH_3CH_2CH(OH)$—unit. Additionally, the correlation of protons (d), (e), and (g) with the amorphous signal for (f) indicated a long unbranched alkyl chain of uncertain length. The carbonyl group connecting these two fragments was confirmed by $^{13}$C NMR spectroscopy (212 ppm) and IR (1709 $cm^{-1}$). GC/MS analysis showed three components (FIG. 8). The major component was assigned to the compound where (f) corresponds to six methylene units (12 H) using both molecular ion and fragmentation information. From these data, we concluded that the predominant molecule in the active fraction was $CH_3CH_2CH(OH)CO(CH_2)_8CH_3$ (3-hydroxytridecan-4-one; stereo-undefined). GC/MS analysis indicated that the active extract also contained minor amounts of molecules where the C10-acyl chain of the thirteen carbon major component is replaced by a C9-acyl or a C8-acyl unit (hereafter abbreviated as C13, C12, and C11).

EXAMPLE 2

Establishing Structure of CAI-1 in *Vibrio*

Chemical Synthesis. All chemicals were purchased from commercial vendors and used without further purification. Unless otherwise noted, all reactions were performed in flame-dried glassware under an atmosphere of argon using dried reagents and solvents. Flash chromatography was performed using standard grade silica gel 60 230-400 mesh from SORBENT Technologies. Thin layer chromatography was carried out using Silica G TLC plates, 200 μm with UV254 (SORBENT Technologies), and visualization was performed by either staining (potassium permanganante or anisaldehyde) and/or by absorbance of UV light.

Synthetic Details. Individual synthesis and biological testing was used to establish the exact structure and biological activity of the potential signaling molecules 5-7. Each of the six hydroxyketones was synthesized according to the reaction series shown in FIG. 7. First, 2-hydroxybutyric acid 1, available commercially in both its pure (R)- and pure (S)-enantiomers, was protected as the tert-butyldiphenylsilyl ether 2 in high yield. The free acid was efficiently converted to the Weinreb amide 3 through CDI-mediated coupling with N,O-dimethylhydroxylamine hydrochloride. The Weinreb amide was then subjected to reaction with an alkyl Grignard reagent; freshly prepared nonyl-, octyl- and heptylmagnesium bromide were used to synthesize compounds 4a-4-c in both the R and S versions. After deprotection of the TBDPS ether using tetrabutylammonium fluoride, final purification of the analogues 5-7 (both pure-R and pure-S) was performed by HPLC (3×25-cm ethyl-pyridine column, 5% EtOAc in hexanes, 30 mL/min, 254 nm, elution at 8 min; followed by a 2×25-cm Premier column, 9:1 hexane:MTBE, 20 mL/min, 280 nm, elution at 15 min). Each compound was thereafter available for biological testing in >99% purity.

The enantio-purity was established by chiral chromatography (Chiralpak AD-H 25×0.46 cm, 15% methanol/$CO_2$ (100 bar), 3 mL/min, 280 nm). For example, isomer 5S showed retention time 2.1 min while the isomer 5R eluted at 3.9 min (see FIG. 11a).

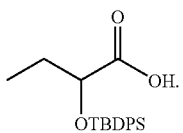

Compound 2

The appropriately protected 2-hydroxybutyric acid derivative 2 was prepared according to the analoguous reported silyl protection of 3-hydroxybutyric acid, as described in Hall, D. R. et al. Identification of components of male-produced pheromone of coffee white stemborer, *Xylotrechus quadripes*. *J. Chem. Ecol.* 32, 195-219 (2006), hereby incorporated by reference into this application. A mixture of imidazole (6.106 g, 89.7 mmol) and TBDPSCl (7 mL, 27.2 mmol) in DMF (6 mL) at 0° C. was added to a stirring solution of 2-hydroxybutyric acid 1 (0.885 g, 8.5 mmol) in DMF (3.5 mL) at 0° C. The reaction mixture was warmed to room temperature and stirred overnight, after which it was poured onto cold saturated sodium chloride (100 mL) and extracted with 5×50 mL 1:3 diethyl ether:petroleum ether. The crude product was washed with water (50 mL), dried over magnesium sulfate, and concentrated. The crude oil was then diluted with 3:2 MeOH:THF (75 mL) and placed at 0° C. Potassium carbonate (2.64 g, 19.1 mmol) dissolved in water (17.5 mL) was added dropwise to solution, which was stirred at room temperature overnight. The solution was then diluted with brine (35 mL), returned to 0° C., and acidified to approximately pH 2 with concentrated sulfuric acid. The acid solution was extracted four times with 1:3 ether:petroleum ether (100 mL). The combined organic layers were washed four times with 2% NaOH (100 mL). The basic layers were combined, placed at 0° C., and reacidified to approximately pH 2 with concentrated sulfuric acid. This aqueous layer was extracted five times with DCM (100 mL). The combined organic layers were dried over MgSO$_4$, filtered, and concentrated to yield 2 as an oily white crystalline solid (2.72 g, 7.9 mmol, 93%). (5)-[α]$_D^{20}$ (deg cm$^3$ g$^{-1}$ dm$^{-1}$)=−31.1 (c=0.014 g cm$^{-3}$ in CHCl$_3$); (R)-[α]$_D^{20}$ (deg cm$^3$ g$^{-1}$ dm$^{-1}$)=+30.0 (c=0.144 g cm$^{-3}$ in CHCl$_3$); $^1$H-NMR (300 MHz, CDCl$_3$) δ p.p.m. 0.97 (t, J=7.44 Hz, 3H), 1.17 (s, 9H), 1.86-1.64 (m, 2H), 4.32 (t, J=5.13 Hz, 1H), 7.49-7.38 (m, 6H), 7.71 (td, J=8.02, 1.71 Hz, 4H), 11.02 (br s, 1H); $^{13}$C-NMR (125 MHz, CDCl$_3$): δ p.p.m. 177.3, 135.8, 135.7, 132.9, 132.5, 130.0, 127.8, 127.7, 73.3, 27.8, 26.9, 19.3, 8.3; IR (CHCl$_3$): 3389, 2965, 2934, 2860, 1773, 1723, 1428 cm$^{-1}$.

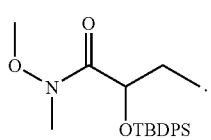

Compound 3

Weinreb amide 3 was derived from the free acid 2 following a synthetic procedure set out for a similar substrate, as described in Sakai, T., Nakagawa, Y., Takahashi, J., Iwabuchi, K., and Ishii, K. Isolation and identification of the male sex pheromone of the grape borer *Xylotrechus pyrrhoderus* Bates (Coleoptera: Cerambycidae). *Chem. Lett.*, 263-264 (1984), hereby incorporated by reference into this application. To a solution of compound 2 (3.13 g, 9.14 mmol) in DCM (19 mL) at 0° C. was added 1,1'-carbonyldiimidazole (2.964 g, 18.3 mmol). After the solution stirred at room temperature overnight, imidazole (1.25 g, 18.3 mmol), DMAP (0.033 g, 0.274 mmol), and N,O-dimethylhydroxylamine hydrochloride (1.78 g, 18.3 mmol) were added at 0° C. The reaction was warmed to room temperature and stirred for 24 hours. The reaction mixture was diluted with DCM (100 mL), washed twice with 2 N HCl (100 mL) and once with brine (50 mL). The organic layer was dried over MgSO$_4$, filtered, concentrated, and purified by silica gel chromatography (20% EtOAc in hexanes; R$_f$(50% EtOAc in hexanes)=0.77) to yield 3 as a white crystalline solid (2.75 g, 7.13 mmol, 78%). (S)-[α]$_D^{20}$ (deg cm$^3$ g$^{-1}$ dm$^{-1}$)=−4.9 (c=0.068 g cm$^3$ in CHCl$_3$); (R)-[α]$_D^{20}$ (deg cm$^3$ g$^{-1}$ dm$^{-1}$)=+4.8 (c=0.044 g cm$^3$ in CHCl$_3$); $^1$H-NMR (400 MHz, CDCl$_3$): δ p.p.m. 0.92 (t, J=7.47 Hz, 3H), 1.10 (s, 9H), 1.82-1.69 (m, 2H), 3.00 (s, 3H), 3.11 (s, 3H), 4.44 (t, J=5.86 Hz, 1H), 7.46-7.33 (m, 6H), 7.71 (td, J=8.03, 1.62 Hz, 4H); $^{13}$C-NMR (125 MHz, CDCl$_3$): δ p.p.m. 136.1, 135.9, 133.9, 133.5, 129.6, 129.5, 127.5, 127.4, 60.6, 27.8, 26.9, 19.4, 9.4; IR (CHCl$_3$): 2972, 1670, 1428 cm$^{-1}$; EIMS (m/z): [M]$^+$ calcd for C$_{22}$H$_{31}$NO$_3$Si, 385. found: 370 (M-Me), 328 (M-$^t$Bu).

Compounds 4a-c were obtained by reaction of the appropriate Grignard reagent with Weinreb amide 3 (as shown for a similar substrate in the literature), as described in Leal, W. S., Shi, X., Nakamuta, K., Ono, M., and Meinwald, J. Structure, stereochemistry, and thermal isomerization of the male sex pheromone of the longhorn beetle *Anaglyptus subfasciatus*. *Proc. Natl. Acad. Sci. USA* 92, 1038-1042 (1995), hereby incorporated by reference into this application.

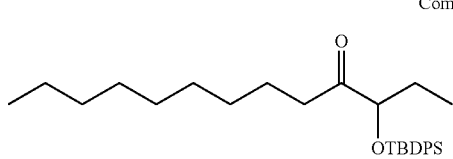

Compound 4a

To a solution of Weinreb amide 3 (1.66 g, 4.5 mmol) in THF (40 mL) at 0° C. was added freshly prepared nonylmagnesium bromide (1.84 M in diethyl ether, 10 mL) dropwise. The reaction mixture was warmed to room temperature and stirred overnight, after which it was diluted with diethyl ether (50 mL), cooled to 0° C., and quenched with water. The organic layer was recovered and washed twice with 10% KHSO$_4$ (50 mL) and once with brine (50 mL). The organic layer was then dried over MgSO$_4$, filtered, concentrated, and purified by silica gel chromatography (2.5% EtOAc in hexanes; R$_f$ (20% EtOAc in hexanes)=0.74) to yield 4a as a yellowed oil (1.76 g, 3.9 mmol, 87%). (S)-[α]$_D^{20}$−(deg cm$^3$ g$^{-1}$dm$^{-1}$)=10.0 (c=0.010 g cm$^{-3}$ in CHCl$_3$); (R)-[α]$_D^{20}$ (deg cm$^3$ g$^{-1}$dm$^{-1}$)=+9.5 (c=0.014 g cm$^{-3}$ in CHCl$_3$); $^1$H-NMR (400 MHz, CDCl$_3$): δ p.p.m. 0.83 (t, J=7.47 Hz, 3H), 0.90 (t, J=6.93 Hz, 3H), 1.13 (s, 9H), 1.35-1.16 (m, 12H), 1.41 (ddd, J=14.54, 6.91, 6.09 Hz, 2H), 1.73-1.51 (m, 2H), 2.53-2.31 (m, 2H), 4.13 (dd, J=6.22, 5.36 Hz, 1H), 7.48-7.34 (m, 6H), 7.64 (dt, J=8.24, 8.15, 1.51 Hz, 4H); $^{13}$C-NMR (125 MHz, CDCl$_3$): δ p.p.m. 212.9, 135.83, 135.79, 133.6, 133.2, 129.83, 129.80, 127.7, 127.6, 80.0, 38.0, 31.9, 29.4, 29.3, 29.2, 27.8, 27.0, 22.9, 22.7, 19.4, 14.1, 8.8; IR (CHCl$_3$): 2975, 2930, 2857, 1711, 1475, 1112 cm$^{-1}$.

Compound 4b

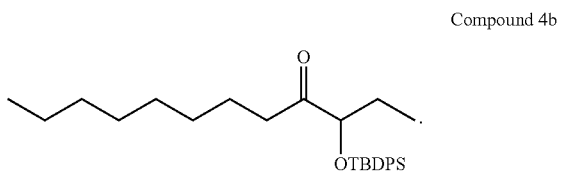

To a solution of Weinreb amide 3 (0.889 g, 2.4 mmol) in THF (13.5 mL) at 0° C. was added freshly prepared octylmagnesium bromide (1.84 M in diethyl ether, 4 mL) dropwise. The reaction mixture was warmed to room temperature and stirred overnight, after which it was diluted with diethyl ether (50 mL), cooled to 0° C., and quenched with water. The organic layer was recovered and washed twice with 10% KHSO$_4$ (50 mL) and once with brine (50 mL). The organic layer was then dried over MgSO$_4$, filtered, concentrated, and purified by silica gel chromatography (2.5% EtOAc in hexanes; R$_f$ (20% EtOAc in hexanes)=0.75) to yield 4b as a yellowed oil (0.829 g, 1.9 mmol, 79%). (S)-[α]$_D^{20}$ (deg cm$^3$ g$^{-1}$dm$^{-1}$)=−19.7 (c=0.033 g cm$^{-3}$ in CHCl$_3$); (R)-[α]$_D^{20}$ (deg cm$^3$ g' dm$^{-1}$)=+20.0 (c=0.027 g cm$^{-3}$ in CHCl$_3$); $^1$H-NMR (500 MHz, CDCl$_3$): δ p.p.m. 0.82 (t, J=7.46 Hz, 3H), 0.89 (t, J=7.04 Hz, 3H), 1.12 (s, 9H), 1.34-1.15 (m, 10H), 1.46-1.34 (m, 2H), 1.72-1.50 (m, 2H), 2.41 (m, 2H), 4.12 (t, J=5.78 Hz, 1H), 7.37 (td, J=13.00, 6.57 Hz, 4H), 7.48-7.40 (m, 2H), 7.66-7.61 (m, 4H); $^{13}$C-NMR (125 MHz, CDCl$_3$): δ p.p.m. 212.9, 135.83, 135.79, 133.7, 133.2, 129.83, 129.81, 127.7, 127.6, 80.0, 38.0, 31.8, 29.4, 29.2, 29.1, 27.8, 27.0, 22.9, 22.6, 19.3, 14.1, 8.8; IR (CHCl$_3$): 2963, 2931, 2858, 1710, 1472, 1112 cm$^{-1}$.

Compound 4c

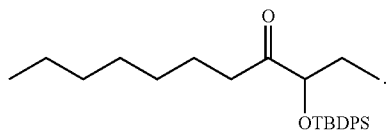

To a solution of Weinreb amide 3 (0.867 g, 2.3 mmol) in THF (13 mL) at 0° C. was added freshly prepared heptylmagnesium bromide (1.82 M in diethyl ether, 4 mL) dropwise. The reaction mixture was warmed to room temperature and stirred overnight, after which it was diluted with diethyl ether (50 mL), cooled to 0° C., and quenched with water. The organic layer was recovered and washed twice with 10% KHSO$_4$ (50 mL) and once with brine (50 mL). The organic layer was then dried over MgSO$_4$, filtered, concentrated, and purified by silica gel chromatography (2.5% EtOAc in hexanes; R$_f$ (20% EtOAc in hexanes)=0.78) to yield 4c as a yellowed oil (0.782 g, 1.9 mmol, 82%). (S)-[α]$_D^{20}$ (deg cm$^3$ g$^{-1}$ dm$^{-1}$)=−24.0 (c=0.023 g cm$^{-3}$ in CHCl$_3$); (R)-[α]$_D^{20}$ (deg cm$^3$ g$^{-1}$ dm$^{-1}$)=+17.5 (c=0.015 g cm$^{-3}$ in CHCl$_3$); $^1$H-NMR (500 MHz, CDCl$_3$): δ p.p.m. 0.81 (t, J=7.47 Hz, 3H), 0.88 (t, J=7.08 Hz, 3H), 1.12 (s, 9H), 1.33-1.14 (m, 8H), 1.47-1.33 (m, 2H), 1.62 (qt, J=13.79, 7.45, 7.37 Hz, 2H), 2.40 (m, 2H), 4.12 (dd, J=6.23, 5.36 Hz, 1H), 7.39-7.34 (m, 4H), 7.45-7.40 (m, 2H), 7.63 (ddd, J=10.30, 8.05, 1.42 Hz, 4H); $^{13}$C-NMR (CDCl$_3$, 125 MHz): δ p.p.m. 212.9, 135.9, 135.8, 133.7, 133.1, 129.9, 129.8, 127.7, 127.6, 80.0, 38.0, 31.7, 29.2, 29.1, 27.8, 27.0, 22.9, 22.6, 19.4, 14.1, 8.8; IR (CHCl$_3$): 2832, 2859, 1711, 1112, 775, 735 cm$^{-1}$.

Compound 5

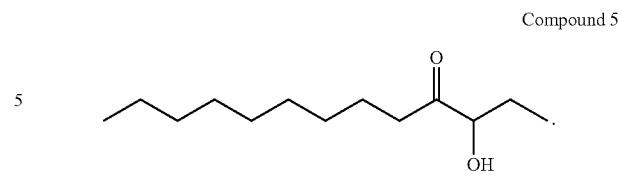

To a solution of protected α-hydroxyketone 4a (0.765 g, 1.7 mmol) in THF (17 mL) at 0° C. was added tetrabutylammonium fluoride (1 M in THF, 5 mL) dropwise. The reaction mixture was warmed to room temperature, and progress of the reaction was monitored by TLC (20% EtOAc in hexanes). Upon full conversion of starting material (product R$_f$=0.47), the reaction mixture was returned to 0° C. and quenched with saturated sodium bicarbonate. The solution was then diluted with diethyl ether (50 mL) and washed with water (10 mL). The organic layer was dried over MgSO$_4$, filtered, concentrated, and purified by HPLC (3×25 ethyl-pyridine column, 5% EtOAc in hexanes, 30 mL/min, 254 nm, elution at 8 min; followed by 2×25 cm Premier column, 9:1 hexane:MTBE, 20 mL/min, 280 nm, elution at 15 min.) (S)-[α]$_D^{20}$ (deg cm$^3$ g$^{-1}$ dm$^{-1}$)=+39.4 (c=0.014 g cm$^{-3}$ in CHCl$_3$); (R)-[α]$_D^{20}$ (deg cm$^3$ g$^{-1}$ dm$^{-1}$)=−35.1 (c=0.026 g cm$^{-3}$ in CHCl$_3$); $^1$H NMR (400 MHz, CDCl$_3$): δ p.p.m. 4.13 (td, J=6.73, 4.47 Hz, 1H), 3.51 (d, J=4.93 Hz, 1H), 2.57-2.30 (m, 2H), 1.88 (dqd, J=14.91, 7.47, 4.04 Hz, 1H), 1.58 (m, 3H), 1.34-1.20 (m, 12H), 0.91 (t, J=7.40, 7.40 Hz, 3H), 0.85 (t, J=6.86 Hz, 3H); $^{13}$C-NMR (100 MHz, CDCl$_3$): δ p.p.m. 212.4, 77.1, 37.8, 31.8, 29.32, 29.29, 29.18, 26.7, 23.5, 22.6, 14.0, 8.8; IR (CHCl$_3$): 3481, 2929, 2855, 1709, 1467, 1075, 983 cm$^{-1}$; EIMS (m/z): [M]$^+$ calcd for C$_{13}$H$_{26}$O$_2$, 214. found 214, 155 (M-COC$_9$H$_{19}$). HRMS (m/z): [M$^+$] calcd for C$_{13}$H$_{26}$O$_2$, 214.19325. found, 214.19359.

Compound 6

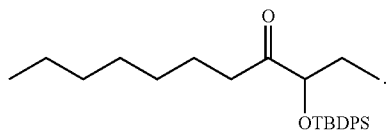

To a solution of protected α-hydroxyketone 4b (0.788 g, 1.8 mmol) in THF (18 mL) at 0° C. was added tetrabutylammonium fluoride (1 M in THF, 5 mL) dropwise. The reaction mixture was warmed to room temperature, and progress of the reaction was monitored by TLC (20% EtOAc in hexanes). Upon full conversion of starting material (product R$_f$=0.45), the reaction mixture was placed at 0° C. and quenched with saturated sodium bicarbonate. The solution was then diluted with diethyl ether (50 mL) and washed with water (10 mL). The organic layer was dried over MgSO$_4$, filtered, concentrated, and purified by HPLC following the conditions described for 5 above. (S)-[α]$_D^{20}$ (deg cm$^3$ g$^{-1}$ dm$^{-1}$)=+58.7 (c=0.022 g cm$^{-3}$ in CHCl$_3$); (R)-[α]$_D^{20}$ (deg cm$^3$ g$^{-1}$ dm$^{-1}$)= −60.8 (c=0.081 g cm$^{-3}$ in CHCl$_3$); $^1$H NMR (500 MHz, CDCl$_3$): δ p.p.m. 4.12 (td, J=6.28, 4.36 Hz, 1H), 3.50 (d, J=4.76 Hz, 1H), 2.49-2.35 (m, 2H), 1.87 (dqd, J=14.92, 7.46, 4.03 Hz, 1H), 1.57 (m, 3H), 1.33-1.18 (m, 10H), 0.91 (t, J=7.40 Hz, 3H), 0.85 (t, J=7.01 Hz, 3H); $^{13}$C-NMR (125 MHz, CDCl$_3$): δ p.p.m. 212.3, 76.6, 37.7, 31.6, 29.14, 29.07, 28.9, 26.6, 23.4, 22.5, 13.9, 8.7; IR (CHCl$_3$): 3486, 2930, 2856, 1709, 1477, 1074, 983 cm$^{-1}$; EIMS (m/z): [M]$^+$ calcd for C$_{12}$H$_{24}$O$_2$, 200. found 200, 141 (M-COC$_8$H$_{17}$).

Compound 7

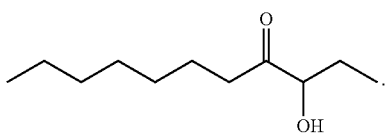

To a solution of protected α-hydroxyketone 4c (0.753 g, 1.8 mmol) in THF (18 mL) at 0° C. was added tetrabutylammonium fluoride (1 M in THF, 5 mL) dropwise. The reaction mixture was warmed to room temperature, and progress of the reaction was monitored by TLC (20% EtOAc in hexanes). Upon full conversion of starting material (product $R_f$=0.45), the reaction mixture was placed at 0° C. and quenched with saturated sodium bicarbonate. The solution was then diluted with diethyl ether (50 mL) and washed with water (10 mL). The organic layer was dried over $MgSO_4$, filtered, concentrated, and purified by HPLC (3×25 ethyl-pyridine column, 5% EtOAc in hexanes, 30 mL/min, 254 nm, elution at 8 min; followed by 2×25 cm Premier column, 9:1 hexane:MTBE, 20 mL/min, 280 nm, elution at 15 min.) (5)-$[\alpha]_D^{20}$ (deg cm$^3$ g$^{-1}$ dm$^{-1}$)=+52.8 (c=0.048 g cm$^{-3}$ in $CHCl_3$); (R)-$[\alpha]_D^{20}$ (deg cm$^3$ g$^{-1}$ dm$^{-1}$)=−51.5 (c=0.012 g cm$^{-3}$ in $CHCl_3$); $^1$H-NMR (500 MHz, $CDCl_3$): δ p.p.m. 4.14 (td, J=6.74, 4.44 Hz, 1H), 3.49 (d, J=4.88 Hz, 1H), 2.54-2.36 (m, 2H), 1.89 (dqd, J=14.93, 7.47, 4.03 Hz, 1H), 1.63 (m, 2H), 1.61 (m, 1H), 1.33-1.22 (m, 8H), 0.93 (t, J=7.40 Hz, 3H), 0.87 (t, J=7.00 Hz, 3H); $^{13}$C-NMR (125 MHz, $CDCl_3$): δ p.p.m. 212.4, 77.1, 37.9, 31.6, 29.2, 29.0, 26.7, 23.6, 22.6, 14.0, 8.8; IR ($CHCl_3$): 3481, 2929, 2858, 1709, 1464, 1405, 1075, 982 cm$^{-1}$; EIMS (m/z): $[M]^+$ calcd for $C_{11}H_{22}O_2$, 186. found: 186, 127 (M-$COC_7H_{15}$).

Figure 3:
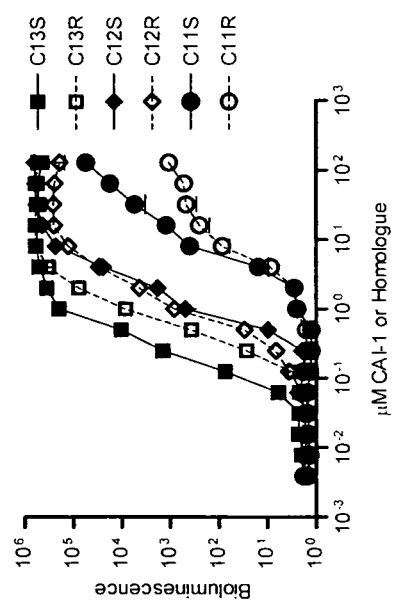
FIG. 3. Activity Profiles for Synthetic CAI-1 and Analogues. S- and R-isomers of synthetic CAI-1 and shorter length analogues identified in the *E. coli* extract were synthesized and tested for the ability to stimulate bioluminescence production (counts per second per 100 μL culture) in the *V. cholerae* CAI-1 reporter strain. Symbols are as follows: (S)- and (R)-3-hydroxytridecan-4-one, filled and open squares, respectively; (S)- and (R)-3-hydroxydodecan-4-one, filled and open diamonds, respectively; (S)- and (R)-3-hydroxyundecan-4-one, filled and open circles, respectively. Error bars represent standard deviations of triplicate samples.

Results. To establish the structure of CAI-1, we synthesized and purified (>99%) each of the six candidates from the above analysis (i.e., R- and S-$CH_3CH_2CH(OH)CO(CH_2)_n$ $CH_3$ where n=6, 7 and 8; see structures 5-7 in FIG. 7). The enantio-purity of each molecule was established by chiral chromatography. We verified that the components in the *E. coli* extract are the C13, C12, and C11 analogues by comparison of GC/MS data with synthetic standards (FIG. 9). Furthermore, using chiral chromatographic methods developed with our synthetic standards, we confirmed that the dominant molecule made by *E. coli* is the S stereoisomer of 3-hydroxytridecan-4-one (FIG. 11). Activity assays of synthetic CAI-1 and analogues support the identification of (S)-3-hydroxytridecan-4-one as CAI-1 (FIG. 3). All six of the synthetic CAI-1 analogues activated the *V. cholerae* quorum sensing circuit to different degrees, following the pattern C13(S)>C13(R)>C12(S)≈C12(R)>C11(S)>C11(R). This ranking shows that the molecules with longer acyl chains are more active than those with shorter acyl chains, and that generally, a compound with S-stereochemistry at the C3 position has superior activity to the counterpart with R stereochemistry. Finally, by capitalizing on the purification and analysis strategies we developed with our synthetic molecules and the *E. coli* extracts, we were able to obtain sufficient activity from *V. cholerae* for analysis. GC/MS and chiral chromatography showed that the only species present in *V. cholerae* culture fluids was the C13 version of the S-isomer, establishing that (S)-3-hydroxytridecan-4-one as the bone fide CAI-1 molecule (FIGS. 10 and 11).

EXAMPLE 3

Controlling Pathogenicity of Vibrios

Western Blot Analysis. *V. cholerae* strains were grown in AKI medium and samples prepared as described previously in Miller et al. (2002). Anti-TcpA antibody and Anti-Rabbit IgG Horseradish Peroxidase Conjugate (Promega) were used with the SuperSignal West Pico Chemiluminescent Substrate (Pierce) system.

Figure 4:
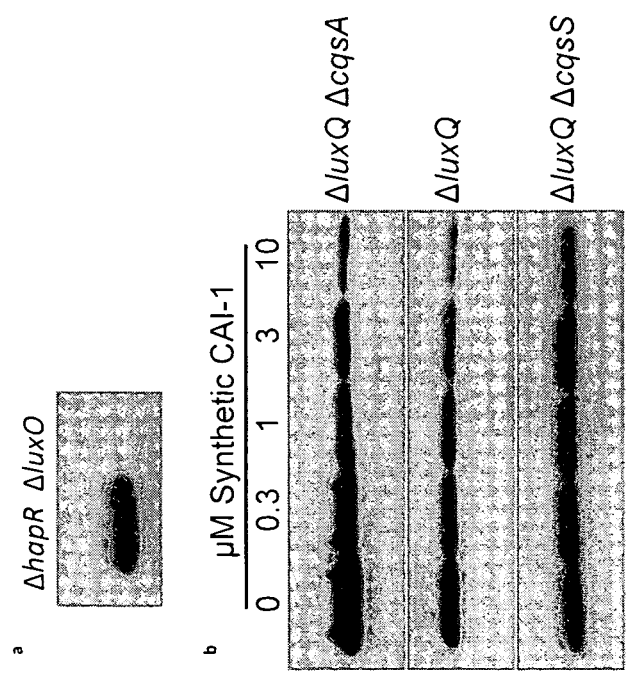
FIG. 4. CAI-1 Inhibits Virulence Factor Expression. Western blots were used to detect TcpA. a, TcpA is produced in the ΔhapR strain that is 'locked' in low-cell-density mode but not in the ΔluxO strain that is 'locked' in high-cell-density mode. b, Increasing concentrations of synthetic CAI-1 repress TcpA production in a *V. cholerae* ΔluxQ, ΔcqsA strain (incapable of responding to AI-2 and incapable of producing CAI-1), top row, a *V. cholerae* ΔluxQ strain (incapable of responding to AI-2 but capable of producing CAI-1), middle row, but not in a *V. cholerae* ΔluxQ, ΔcqsS strain (incapable of responding to both AI-2 and CAI-1), bottom row.

Results. A major goal of quorum-sensing research is to develop strategies to artificially manipulate quorum-sensing-controlled processes in bacteria. Toward this end, *V. cholerae* was treated with synthetic CAI-1 and examination was made of the consequences on production of TcpA. TcpA, a subunit of the toxin co-regulated pilus (TCP), is a primary host colonization factor, as described in Taylor, R. K., Miller, V. L., Furlong, D. B., and Mekalanos, J. J. Use of phoA gene fusions to identify a pilus colonization factor coordinately regulated with cholera toxin. *Proc. Natl. Acad. Sci. USA* 84, 2833-2837 (1987), hereby incorporated by reference into this application. Consistent with earlier results showing that virulence factors are expressed at low-cell density and repressed by autoinducers at high-cell density, high-level production of TCP occurred in *V. cholerae* mutants 'locked' in low-cell-density mode (ΔhapR) whereas cells 'locked' in high-cell-density mode (ΔluxO) produced no TcpA (FIG. 4a and see FIG. 1), as described in Miller et al. (2002) and Zhu et al. (2002). The addition of synthetic CAI-1 at concentrations up to 10 μM substantially repressed TcpA production in a ΔluxQ, ΔcqsA *V. cholerae* strain that cannot respond to AI-2 or produce CAI-1 (FIG. 4b, top row). Although less dramatic, TcpA levels also decreased when CAI-1 was provided to the ΔluxQ, cqsA$^+$ strain (FIG. 4b, middle row). Together, these results show that exogenously supplied synthetic CAI-1 is capable of controlling gene expression in *V. cholerae* both in the absence and presence of endogenously produced CAI-1. Importantly, synthetic CAI-1 had no effect on TcpA production in a ΔluxQ, ΔcqsS strain, which cannot respond to either CAI-1 or AI-2 (FIG. 4b, bottom row). This final result demonstrates that information flow through the *V. cholerae* quorum-sensing circuit is absolutely required for CAI-1 repression of TCP production, and, we infer, repression of other virulence factors.

EXAMPLE 4

CAI-1 Thermal Stability

Figure 6:
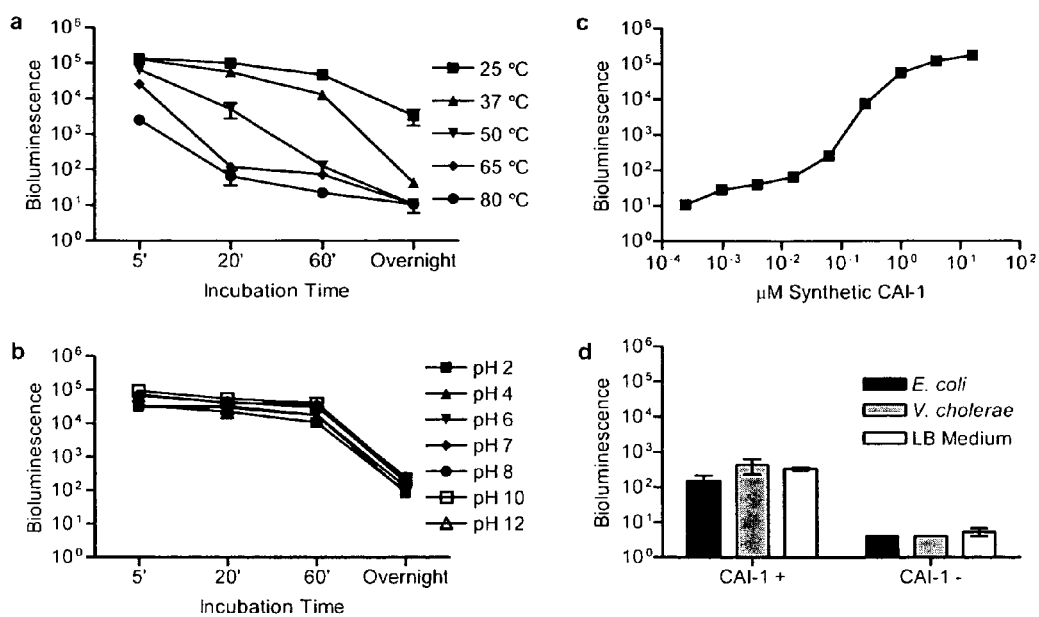
FIG. 6. Analysis of CAI-1 Stability. a, CAI-1 is heat stable at physiologically relevant temperatures, but subject to degradation at high temperatures. Buffered synthetic CAI-1 was incubated at 25° C. (squares), 37° C. (triangles), 50° C. (inverted triangles), 65° C. (diamonds), and 80° C. (circles) for 5, 20, 60 minutes, or overnight. *V. cholerae* bioluminescence reporter assay performed as described in Example 1. In each assay, final CAI-1 concentration was 3.3 μM. Bioluminescence units are counts per second per 100 μL culture. Error bars denote standard deviations of triplicate bioassay samples. b, CAI-1 is stable under a wide range of pH values. The autoinducer was incubated at pH 2, 4, 6, 7, 8, 10, and 12 in potassium phosphate buffer (closed squares, closed triangles, inverted triangles, diamonds, circles, open squares, open triangles, respectively) for 5, 20, 60 minutes, or overnight before being neutralized (see Methods). Reporter bioassay and error bars as in a. c, CAI-1 standard curve for comparison of activities. Reporter bioassay and error bars as in a and FIG. 3. d, *E. coli* and *V. cholerae* (autoinducer production mutant) cells do not adversely affect CAI-1 levels. Log phase *E. coli* ΔluxS and *V. cholerae* ΔluxS ΔcqsA cells in LB medium along with sterile LB medium were shaken at 37° C. overnight with and without 10 μM CAI-1 supplement. Reporter bioassay and error bars as in a, with a 1 uM concentration of CAI-1. Assay showed equal activities in cells treated with autoinducer (black bars, *E. coli*; gray bars, *V. cholerae*) as in sterile medium with autoinducer (white bars) "CAI+". This activity was not present in samples incubated without autoinducer supplementation "CAI-1-".

CAI-1 stock in DMSO was diluted 1:128 into 10 mM potassium phosphate buffer at pH 7 to a final autoinducer concentration of 400 μM. Samples were incubated for specified lengths of time, chilled briefly on ice, and frozen in dry ice/ethanol. Samples were thawed, diluted 1:3 in the same phosphate buffer, and read with the *V. cholerae* bioluminescence assay. Diluted sample was added at 2.5% of reporter culture volume, for final concentrations of 3.3 μM CAI-1 and 250 μM potassium phosphate. Results are shown in FIG. 6A.

EXAMPLE 5

CAI-1 pH Stability

CAI-1 stock in DMSO was diluted 1:128 into 100 mM potassium phosphate buffer at specified pH values to a final autoinducer concentration of 400 μM. Following incubation at room temperature for specified times, samples were neutralized with an equal volume of 100 mM potassium phosphate buffer (e.g. pH 10 buffer was added to pH 4 buffered autoinducer). Neutralized samples, now with 200 μM CAI-1, were chilled briefly on ice and frozen in dry ice/ethanol. Autoinducer samples were thawed, diluted 1:3 in 100 mM pH 7 potassium phosphate buffer, and read with the *V. cholerae* bioluminescence assay. Diluted sample was added at 5% of reporter culture volume, for final concentrations of 3.3 µM CAI-1 and 5 mM potassium phosphate. Results are shown in FIG. 6B.

EXAMPLE 6

CAI-1 Stability in Culture

Early stationary phase *E. coli* KX1200 (MG1655 ΔluxS) and *V. cholerae* BH1575 (El Tor C6706str ΔluxS ΔcqsA) were diluted to OD 0.1 in LB medium. Along with sterile LB medium, they were shaken overnight at 37° C. with and without 10 µM CAI-1 supplementation. Culture and LB samples were centrifuged at 10,000×g, filtered with 0.22 µm filters, and read at 10% final culture volume using the *V. cholerae* CAI-1 reporter bioassay. Results are shown in FIG. 6D.

EXAMPLE 7

Effect of Synthetic Autoinducers on Colonization of *Vibrio cholerae* in Infant Mice Methods. Wild type *Vibrio cholerae* El Tor C6706 were grown to saturation ($5 \times 10^9$ CFU/ml) in LB medium at 30° C. with shaking Cell density was adjusted to $\sim 5 \times 10^6$ CFU/ml with LB medium. Diluted *V. cholerae* culture was treated with or without 20 µM CAI-1 ((S)-3-hydroxytridecan-4-one) (in DMSO) and 20 µM DPD ((S)-4,5-dihydroxypentane-2,3-dione) (in $NaPO_4$ buffer) for 30 minutes at 30° C. CD1 infant mice (5 and 6-day-old) were infected orally with $2.5 \times 10^5$ CFU (in 50 µl) of *V. cholerae* treated with or without autoinducers. Two and five hours post-infection, animals that were infected with autoinducer-treated *V. cholerae* received orally 50 µA of solution containing 3 mM CAI-1 and 0.5 mM DPD. Animals that were infected with non-autoinducer-treated *V. cholerae* received an identical solution except autoinducers were omitted. Seven hours post-infection, animals were euthanized and the intestinal portions between the stomach and the caecum were surgically removed and mechanically homogenized. *V. cholerae* from the intestinal homogenate were counted by plating on selective medium.

Results. Synthetic autoinducers repress expression of *V. cholerae* colonization factor TCP in vitro (Example 3). As a further indication of the therapeutic effect of autoinducer, an experiment was conducted to determine if synthetic autoinducers would reduce *V. cholerae* colonization in a host. Using a well-established infant mouse colonization assay, the data collected showed that autoinducers decrease the total viable count of wild type *V. cholerae* in the intestine by an average of 20-fold. The results are shown in FIG. 12. This result indicated that synthetic autoinducers reduce the ability of *V. cholerae* to colonize the host and shows utility for the use as an anti-cholera treatment.

EXAMPLE 8

Preparation of Synthetic Autoinducers and Test of Activity

CAI-1 analogues were dissolved in DMSO and supplied at 0.5% total volume to the CAI-1 reporter strain MM920 (*V. cholerae* El Tor C6706strΔcqsAΔluxQpBB1 (luxCDABE from V. harveyi). Bioluminescence measurements at varying concentrations of analogue (generally from $10^{-3}$ µM to $10^{-2}$ µM) were measured using a Wallac EnVision 2103 Multilabel Reader (Perkin Elmer, Waltham, Mass.).

CAI-1 analogues and their activity are shown in FIG. 13. As a measurable indication of activity, a reporter strain provided for measurements of bioluminescence as a percentage of the bioluminescence activity of the *V. cholerae* CAI-1 autoinducer. The reference compound, (S)-3-hydroxytridecan-4-one, is the natural autoinducer, CAI-1. Compound 22 3-aminotridecan-4-one hydrochloride exhibits equivalent activity to CAI-1. Compound 7 (R)-3-hydroxytridecan-4-one exhibits forty percent of the activity of CAI-1. Compounds 5 and 6, (S)-3-hydroxydodecan-4-one and (R)-3-hydroxydodecan-4-one, exhibit twenty percent of the activity of CAI-1. Compound 10, tridecane-3,4-dione, exhibits ten percent of the activity of CAI-1. Compounds 3, 4, 12, and 13 all exhibit less than five percent of the activity of CAI-1.

The examples and representative species described herein are for illustrative purposes and are not meant to limit the scope of the invention. From the foregoing description, it will be apparent that variations and modifications may be made to the invention described herein to adopt it to various usages and conditions. Such embodiments are also within the scope of the following claims.

The invention claimed is:
1. A purified compound that is (S)-3-hydroxytridecan-4-one, (R)-3-hydroxytridecan-4-one, (S)-3-hydroxydodecan-4-one, (R)-3-hydroxydodecan-4-one, (S)-3-hydroxyundecan-4-one, or (R)-3-hydroxyundecan-4-one.
2. A composition comprising the compound of claim 1 wherein the composition inhibits biofilm formation.
3. A composition comprising at least one compound recited in claim 1 wherein the composition inhibits virulence in *V. cholerae*.
4. A method of inhibiting quorum-sensing-dependent activity in *Vibrio* spp. comprising contacting the *Vibrio* bacteria with an effective amount of the compound of claim 1.
5. The method of claim 4 wherein the quorum-sensing-dependent activity is bio film formation.
6. The method of claim 4 wherein the quorum-sensing-dependent activity is pathogenicity.
7. The method of claim 6 wherein the pathogenicity is caused by production of a virulence factor that comprises TCP.
8. The method of claim 4 wherein the bacteria are *V. cholerae*, *V. harveyi*, *V. anguillarum*, *V. alginolyticus*, *V. parahaemolyticus*, *V. furnissi*, *V. angustum*, *V. proteolyticus* or *V. vulnificus*.
9. The method of claim 4 wherein the bacteria are *V. campbelli*, *V. spledidus*, or *V. shilonii*.
10. A pharmaceutical composition comprising the compound of claim 1 and a pharmaceutically acceptable carrier, excipient or diluent.
11. A method for repressing *V. cholerae* pathogenicity comprising contacting *V. cholerae* bacteria with the compound of claims 1 and (S)-4,5-dihydroxypentane-2,3-dione (DPD).
12. A method for repressing *V. cholerae* pathogenicity comprising contacting *V. cholerae* bacteria with (S)-3-hydroxytridecan-4-one (CAI-1) and (S)-4,5-dihydroxypentane-2,3-dione (DPD).
13. A composition for use in the treatment of cholera in a subject wherein said composition comprises the compound of claim 1 with a diluent or carrier.
14. A purified compound that is (S)-3-hydroxydodecan-4-one, (R)-3-hydroxydodecan-4-one, (S)-3-hydroxyundecan-4-one, or (R)-3-hydroxyundecan-4-one.

* * * * *